(12) United States Patent
Hardie et al.

(10) Patent No.: US 10,993,848 B2
(45) Date of Patent: May 4, 2021

(54) DISCREET DISPOSABLE ABSORBENT ARTICLE

(71) Applicant: The Procter & Gamble Company, Cincinnati, OH (US)

(72) Inventors: Stephen Lebeuf Hardie, Mason, OH (US); Ronda Lynn Glassmeyer, Cincinnati, OH (US); Edward Paul Carlin, Deerfield Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 523 days.

(21) Appl. No.: 15/729,792

(22) Filed: Oct. 11, 2017

(65) Prior Publication Data

US 2018/0098889 A1 Apr. 12, 2018

Related U.S. Application Data

(60) Provisional application No. 62/406,716, filed on Oct. 11, 2016.

(51) Int. Cl.
*A61F 13/511* (2006.01)
*A61F 13/514* (2006.01)
(Continued)

(52) U.S. Cl.
CPC ...... *A61F 13/475* (2013.01); *A61F 13/15203* (2013.01); *A61F 13/47* (2013.01);
(Continued)

(58) Field of Classification Search
CPC .............. A61F 13/475; A61F 13/15203; A61F 2013/15463; A61F 2013/530481
See application file for complete search history.

(56) References Cited

U.S. PATENT DOCUMENTS

| 1,946,626 | A | 2/1934 | Jurgensen |
| 2,296,341 | A | 9/1942 | Fourness |

(Continued)

FOREIGN PATENT DOCUMENTS

| EP | 2 901 992 B1 | 12/2016 |
| WO | WO200059438 A1 | 10/2000 |

(Continued)

OTHER PUBLICATIONS

All Office Actions for U.S. Appl. No. 15/729,870.
All Office Actions for U.S. Appl. No. 15/729,839.
PCT International Search Report, dated Nov. 27, 2017, 232 pages.

*Primary Examiner* — Adam Marcetich
*Assistant Examiner* — Meagan Ngo
(74) *Attorney, Agent, or Firm* — George H. Leal; Dara M. Kendall

(57) ABSTRACT

Disposable absorbent articles suitable for providing leakage protection for users that experience relatively small to relatively large discharges of fluids wherein the article comprises a chassis which comprises a primary topsheet; a backsheet; an absorbent core having a front end portion, a central portion, and a rear end portion along its length, the core being disposed between the primary topsheet and the backsheet, and the article exhibits an article length of from about 371 mm to about 500 mm according to the Article Length Method; an Acquisition Time for a load of 60 ml of less than about 39 seconds according to a Speed of Acquisition with Balloon Applied Pressure Method; a dry pad thickness of between about 4.6 mm to about 12 mm according to a Pad Thickness Method; and an Energy of Recovery at a load of 30 ml of from about 4 mJ to about 11 mJ according to a Bunch Compression Method.

25 Claims, 10 Drawing Sheets

(51) Int. Cl.
*A61F 13/53* (2006.01)
*A61F 13/49* (2006.01)
*A61F 13/475* (2006.01)
*A61F 13/535* (2006.01)
*A61F 13/537* (2006.01)
*A61F 13/15* (2006.01)
*A61F 13/472* (2006.01)
*A61F 13/534* (2006.01)
*A61F 13/56* (2006.01)
*A61L 15/22* (2006.01)
*A61F 13/47* (2006.01)
*A41B 9/12* (2006.01)

(52) U.S. Cl.
CPC ........ *A61F 13/472* (2013.01); *A61F 13/4758* (2013.01); *A61F 13/514* (2013.01); *A61F 13/51121* (2013.01); *A61F 13/534* (2013.01); *A61F 13/535* (2013.01); *A61F 13/537* (2013.01); *A61F 13/53409* (2013.01); *A61F 13/5611* (2013.01); *A61L 15/225* (2013.01); *A41B 9/12* (2013.01); *A61F 13/49* (2013.01); *A61F 13/49009* (2013.01); *A61F 2013/15121* (2013.01); *A61F 2013/15292* (2013.01); *A61F 2013/15357* (2013.01); *A61F 2013/15365* (2013.01); *A61F 2013/15406* (2013.01); *A61F 2013/15463* (2013.01); *A61F 2013/15487* (2013.01); *A61F 2013/53024* (2013.01); *A61F 2013/5355* (2013.01); *A61F 2013/530233* (2013.01); *A61F 2013/530248* (2013.01); *A61F 2013/530481* (2013.01); *A61F 2013/530613* (2013.01)

(56) References Cited

U.S. PATENT DOCUMENTS

| | | |
|---|---|---|
| 3,386,442 A | 6/1968 | Sabee |
| 3,406,688 A | 10/1968 | Cubitt |
| 3,431,911 A | 3/1969 | Meisel, Jr. |
| 3,528,421 A | 9/1970 | Vaillancourt et al. |
| 3,572,342 A | 3/1971 | Lindquist et al. |
| 3,604,422 A | 9/1971 | Sabee |
| 3,651,809 A | 3/1972 | Champaigne, Jr. |
| 3,695,269 A | 10/1972 | Malaney |
| 3,799,167 A | 3/1974 | Miller et al. |
| 3,805,790 A | 4/1974 | Kaczmarzyk et al. |
| 3,815,602 A | 6/1974 | Johns et al. |
| 3,825,006 A | 7/1974 | Ralph |
| 3,838,693 A | 10/1974 | Sherman |
| 3,871,037 A | 3/1975 | Willington |
| 3,954,721 A | 5/1976 | Gross |
| 3,983,095 A | 9/1976 | Bashaw et al. |
| 3,996,936 A | 12/1976 | Widlund et al. |
| 4,047,531 A | 9/1977 | Karami |
| 4,102,340 A | 7/1978 | Mesek et al. |
| 4,136,697 A | 1/1979 | Smith |
| 4,211,227 A | 7/1980 | Anderson et al. |
| 4,231,357 A | 11/1980 | Hessner |
| 4,269,188 A | 5/1981 | Nishizawa et al. |
| 4,282,874 A | 8/1981 | Mesek |
| 4,285,342 A | 8/1981 | Mesek |
| 4,333,464 A | 6/1982 | Nakano |
| 4,333,465 A | 6/1982 | Wiegner |
| 4,335,722 A | 6/1982 | Jackson |
| 4,338,371 A | 7/1982 | Dawn et al. |
| 4,354,901 A | 10/1982 | Kopolow |
| 4,364,992 A | 12/1982 | Ito et al. |
| 4,381,783 A | 5/1983 | Elias |
| 4,397,644 A | 8/1983 | Matthews et al. |
| 4,410,324 A | 10/1983 | Sabee |
| 4,411,660 A | 10/1983 | Dawn et al. |
| 4,480,000 A | 10/1984 | Watanabe et al. |
| 4,500,315 A | 2/1985 | Pieniak et al. |
| 4,536,181 A | 8/1985 | Cook |
| 4,537,590 A | 8/1985 | Pieniak et al. |
| 4,557,777 A | 12/1985 | Sabee |
| 4,560,372 A | 12/1985 | Pieniak |
| 4,560,379 A | 12/1985 | Stemmler |
| 4,610,678 A | 9/1986 | Weisman |
| 4,655,757 A | 4/1987 | McFarland et al. |
| 4,666,439 A | 5/1987 | Williams et al. |
| 4,673,402 A | 6/1987 | Weisman et al. |
| 4,676,784 A | 6/1987 | Erdman et al. |
| 4,685,914 A | 8/1987 | Holtman |
| 4,699,823 A | 10/1987 | Kellenberger et al. |
| 4,710,187 A | 12/1987 | Boland et al. |
| 4,762,521 A | 8/1988 | Roessler et al. |
| 4,770,656 A | 9/1988 | Proxmire et al. |
| 4,781,711 A | 11/1988 | Houghton et al. |
| 4,790,839 A | 12/1988 | Ahr |
| 4,798,603 A | 1/1989 | Meyer et al. |
| 4,806,408 A | 2/1989 | Pierre et al. |
| 4,888,093 A | 12/1989 | Dean et al. |
| 4,888,238 A | 12/1989 | Katz et al. |
| 4,900,318 A | 2/1990 | Toth |
| 4,911,700 A | 3/1990 | Makoui et al. |
| 4,923,454 A | 5/1990 | Seymour et al. |
| 4,935,022 A | 6/1990 | Lash et al. |
| 4,944,735 A | 7/1990 | Mokry |
| 4,973,325 A | 11/1990 | Sherrod et al. |
| 4,988,344 A | 1/1991 | Reising et al. |
| 4,988,345 A | 1/1991 | Reising |
| 4,990,147 A | 2/1991 | Freeland |
| 5,009,650 A | 4/1991 | Bernardin |
| 5,013,309 A | 5/1991 | Baigas, Jr. et al. |
| 5,037,409 A | 8/1991 | Chen et al. |
| 5,061,259 A | 10/1991 | Goldman et al. |
| 5,061,260 A | 10/1991 | Callahan |
| 5,069,676 A | 12/1991 | Ito et al. |
| 5,079,004 A | 1/1992 | Blank et al. |
| 5,087,506 A | 2/1992 | Palumbo |
| 5,098,422 A | 3/1992 | Davis et al. |
| 5,134,007 A | 7/1992 | Reising et al. |
| 5,147,343 A | 9/1992 | Kellenberger |
| 5,147,345 A | 9/1992 | Kellenberger et al. |
| 5,149,335 A | 9/1992 | Kellenberger et al. |
| 5,176,668 A | 1/1993 | Bernardin |
| 5,192,606 A | 3/1993 | Proxmire et al. |
| 5,294,478 A | 3/1994 | Wanek et al. |
| 5,300,053 A | 4/1994 | Genaro |
| 5,300,054 A | 4/1994 | Feist et al. |
| 5,304,161 A | 4/1994 | Noel et al. |
| 5,387,207 A | 2/1995 | Dyer et al. |
| 5,411,497 A | 5/1995 | Tanzer et al. |
| 5,425,725 A | 6/1995 | Tanzer et al. |
| 5,433,715 A | 7/1995 | Tanzer et al. |
| 5,440,061 A | 8/1995 | Gibson |
| 5,454,800 A * | 10/1995 | Hirt ............... A61F 13/53427 604/358 |
| 5,466,513 A | 11/1995 | Wanek et al. |
| 5,509,915 A | 4/1996 | Hanson et al. |
| 5,700,254 A * | 12/1997 | McDowall ........ A61F 13/15617 604/378 |
| 5,830,202 A | 11/1998 | Bogdanski et al. |
| 6,068,620 A * | 5/2000 | Chmielewski .... A61F 13/15658 604/358 |
| 9,238,089 B2 | 1/2016 | Chmielewski et al. |
| 2003/0225384 A1 | 12/2003 | Zenker et al. |
| 2004/0015142 A1 | 1/2004 | Johnston |
| 2006/0069367 A1 | 3/2006 | Waksmundzki |
| 2007/0005037 A1* | 1/2007 | Mansfield ......... A61F 13/49015 604/385.3 |
| 2007/0249254 A1* | 10/2007 | Mansfield ............. B32B 25/10 442/399 |
| 2007/0250031 A1* | 10/2007 | Woltman ............ A61F 13/5514 604/385.201 |
| 2012/0238984 A1* | 9/2012 | Paldey ............. A61F 13/53708 604/378 |
| 2014/0005623 A1 | 1/2014 | Wirtz et al. |
| 2014/0163500 A1 | 6/2014 | Roe et al. |

(56) References Cited

U.S. PATENT DOCUMENTS

| | | | |
|---|---|---|---|
| 2014/0163501 A1* | 6/2014 | Ehrnsperger | A61F 13/4753 604/366 |
| 2014/0257219 A1* | 9/2014 | Neton | A61F 13/51401 604/365 |
| 2015/0238369 A1* | 8/2015 | Kaiser | A61F 13/15634 604/375 |
| 2018/0098889 A1 | 4/2018 | Hardie et al. | |
| 2018/0098890 A1 | 4/2018 | Hardie et al. | |
| 2018/0098891 A1 | 4/2018 | Hardie et al. | |

FOREIGN PATENT DOCUMENTS

| WO | WO2011056205 A1 | 5/2011 |
|---|---|---|
| WO | WO2013180937 A1 | 12/2013 |

* cited by examiner

DISCREET DISPOSABLE ABSORBENT ARTICLE

FIELD

The present invention pertains to discreet disposable absorbent articles suitable for absorbing and containing body exudates.

BACKGROUND

A variety of disposable absorbent articles have been relied on by consumers to handle or manage body exudates. These consumers may include babies, toddlers, children, teenagers, adults, and elderly persons. Thus, it is clear that the types of fluids or body exudates managed by such articles may vary as well to include urine, feces, menses, and other discharges. Typically, in the case of adults, the articles take the form of sanitary napkins, adult incontinence pads, and adult incontinence diapers or undergarments. One of the primary drivers of the desirability of these products to wearers is to give them assurance that when they experience incontinence, the occurrence of such will go unnoticed by others and even more ideally by the wearers.

One way of improving the performance and overall discretion of disposable absorbent articles that has been widely utilized by manufacturers has been the inclusion of superabsorbent polymers which are able to intake increased amounts of liquid and consequently form a swollen hydrogel material. The resulting hydrogel serves to retain fluid such as discharged body liquids within the structure. An absorbent structure of this type wherein hydrogel-forming materials in particulate form are incorporated into fibrous webs is disclosed in Weisman and Goldman; U.S. Pat. No. 4,610,678; issued Sep. 9, 1986.

While disposable absorbent articles with these superabsorbent materials tend to be highly absorbent and less bulky, there are a number of users of these products that have a relatively high body mass index (BMI) (i.e., about 25 or greater) for which these products still leave much to be desired. In particular, these users tend to experience exaggerated bunching of the absorbent article during wear and as a result there can be increased opportunity for leaks to occur.

Consequently, there is a need for a disposable absorbent article which targets to provide increased protection from leakage to consumers which have a relatively high BMI while maintaining a level of discretion to the wearer while in use. There is also a need for designers of such an article to take into account the perceived absorbency needs of these consumers as well even when the overall volume to be absorbed is relatively light to moderate.

SUMMARY

Disposable absorbent articles in accordance with the present invention are well suited for providing leakage protection for users that experience relatively small to relatively large discharges of fluids. In an embodiment, an absorbent article comprises a primary topsheet having a body-facing surface and a garment-facing surface; a backsheet having a body-facing surface and garment-facing surface; an absorbent core having a front end portion, a central portion, and a rear end portion along its length, said core being disposed between said primary topsheet garment-facing surface and said backsheet body-facing surface, and the article exhibits an article length of from about 371 mm to about 500 mm according to the Article Length Method; an Acquisition Time for a load of 60 ml of less than about 39 seconds according to a Speed of Acquisition with Balloon Applied Pressure Method; a dry pad thickness of between about 4.6 mm to about 12 mm according to a Pad Thickness Method; and an Energy of Recovery at a load of 30 ml of from about 4 mJ to about 11 mJ according to a Bunch Compression Method.

A second embodiment is directed to an absorbent article comprising a chassis which comprises a primary topsheet having a body-facing surface and a garment-facing surface; a backsheet having a body-facing surface and garment-facing surface; an absorbent core which is disposed between said primary topsheet garment-facing surface and said backsheet body-facing surface, wherein said core comprises a first laminate having a first end which is complementary in shape to a respective second end, the first laminate comprises a first superabsorbent layer disposed onto a first distribution layer; and the article exhibits an article length of from about 371 mm to about 500 mm according to the Article Length Method; an Acquisition Time for a load of 60 ml of less than about 39 seconds according to a Speed of Acquisition with Balloon Applied Pressure Method; a dry pad thickness of between about 4.6 mm to about 12 mm according to a Pad Thickness Method; and an Energy of Recovery at a load of 30 ml of from about 4 mJ to about 11 mJ according to a Bunch Compression Method.

A third embodiment is further directed to an absorbent article comprising a chassis which comprises a primary topsheet having a body-facing surface and a garment-facing surface; a backsheet having a body-facing surface and garment-facing surface; an absorbent core which is disposed between said primary topsheet garment-facing surface and said backsheet body-facing surface, wherein said core comprises 1) a first laminate which includes a first superabsorbent layer disposed onto a first distribution layer and 2) a second laminate which includes a second distribution layer joined to a second superabsorbent layer; wherein said first distribution layer is joined to said second distribution layer along a length of the absorbent article wherein one of the first or second laminates has a larger cross-direction width than the other and the article exhibits an article length of from about 371 mm to about 500 mm according to the Article Length Method; an Acquisition Time for a load of 60 ml of less than about 39 seconds according to a Speed of Acquisition with Balloon Applied Pressure Method; a dry pad thickness of between about 4.6 mm to about 12 mm according to a Pad Thickness Method; and an Energy of Recovery at a load of 30 ml of from about 4 mJ to about 11 mJ according to a Bunch Compression Method.

A fourth embodiment relates to an absorbent article comprising a chassis which comprises a primary topsheet having a body-facing surface and a garment-facing surface; a backsheet having a body-facing surface and garment-facing surface; an absorbent core which is disposed between said primary topsheet garment-facing surface and said backsheet body-facing surface, wherein said core comprises a first laminate which includes a first superabsorbent layer disposed discontinuously onto a first distribution layer and a second laminate which includes a second distribution layer joined to a second superabsorbent layer; wherein said first distribution layer is joined to said second distribution layer and the article exhibits an article length of from about 371 mm to about 500 mm according to the Article Length Method; an Acquisition Time for a load of 60 ml of less than about 39 seconds according to a Speed of Acquisition with Balloon Applied Pressure Method; a dry pad thickness of between about 4.6 mm to about 12 mm according to a Pad Thickness Method; and an Energy of Recovery at a load of 30 ml of from about 4 mJ to about 11 mJ according to a Bunch Compression Method.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which the designations are used to designate substantially identical elements and in which:

DETAILED DESCRIPTION

The disposable absorbent articles, particularly incontinence pads or pants, of the present invention can provide flexibility to allow for an improved and comfortable fit which is less susceptible to bunching during use. In particular, it is envisioned that the articles of the present invention exhibit heightened structural resiliency from the proposed configuration and orientation of the layers contained therein. For the purposes of this disclosure, reference to an incontinence pad, disposable absorbent article, or absorbent article will be used. However, the present invention may be applied to a plurality of absorbent articles including, but not limited to, sanitary napkins, pantiliners, menstrual pads, diapers, training pants, adult incontinence pants, etc.

There are several factors to consider when designing a disposable absorbent article like an incontinence pad, particularly if improved fit and performance are desired. First, the stiffness of the pad is an important factor. Typically, thinner pads offer less stiffness than their bulkier counterparts. While bulkier pads may be less likely to succumb to the compression that is typical during wear, bulkier pads are less desirable because they can cause the incontinence pad to lose its discreetness during use. Furthermore, some flexibility in the absorbent core can allow the incontinence pad to adjust more readily to the contours of the body of a user during use. Second, the absorbency of the pad is key in determining whether or not the pad is useful for consumers. Ideally, the pad is well suited to accommodate either small or large loads of exudates. This accommodation means not only storing either type of load sufficiently but also effectively and quickly wicking such loads from a body-contacting surface of the pad such that the user experiences little to no feeling of wetness after the release of the load. In the case of a small load, a wearer should be able to continue to wear the pad for some reasonable time after a release since immediate changing of the pad may not be feasible or desired.

In the past, incontinence pad designs have required a bit of compromise relative to these factors. In contrast, the absorbent articles, which include but are not limited to incontinence, designed pursuant to the present invention account for these factors to arrive at an absorbent article which exhibits improved protection against leakage, particularly for those wearers of a higher than average body mass index (BMI). Namely, incontinence pads of the present invention provide good core flexibility, excellent wicking, distribution, and overall absorbency, and in certain embodiments, may include barrier cuffs which stand up during use and contact the wearer in an appropriate location are included as part of the construction to further protect against a likelihood of leakage from the pad.

Figure 1:
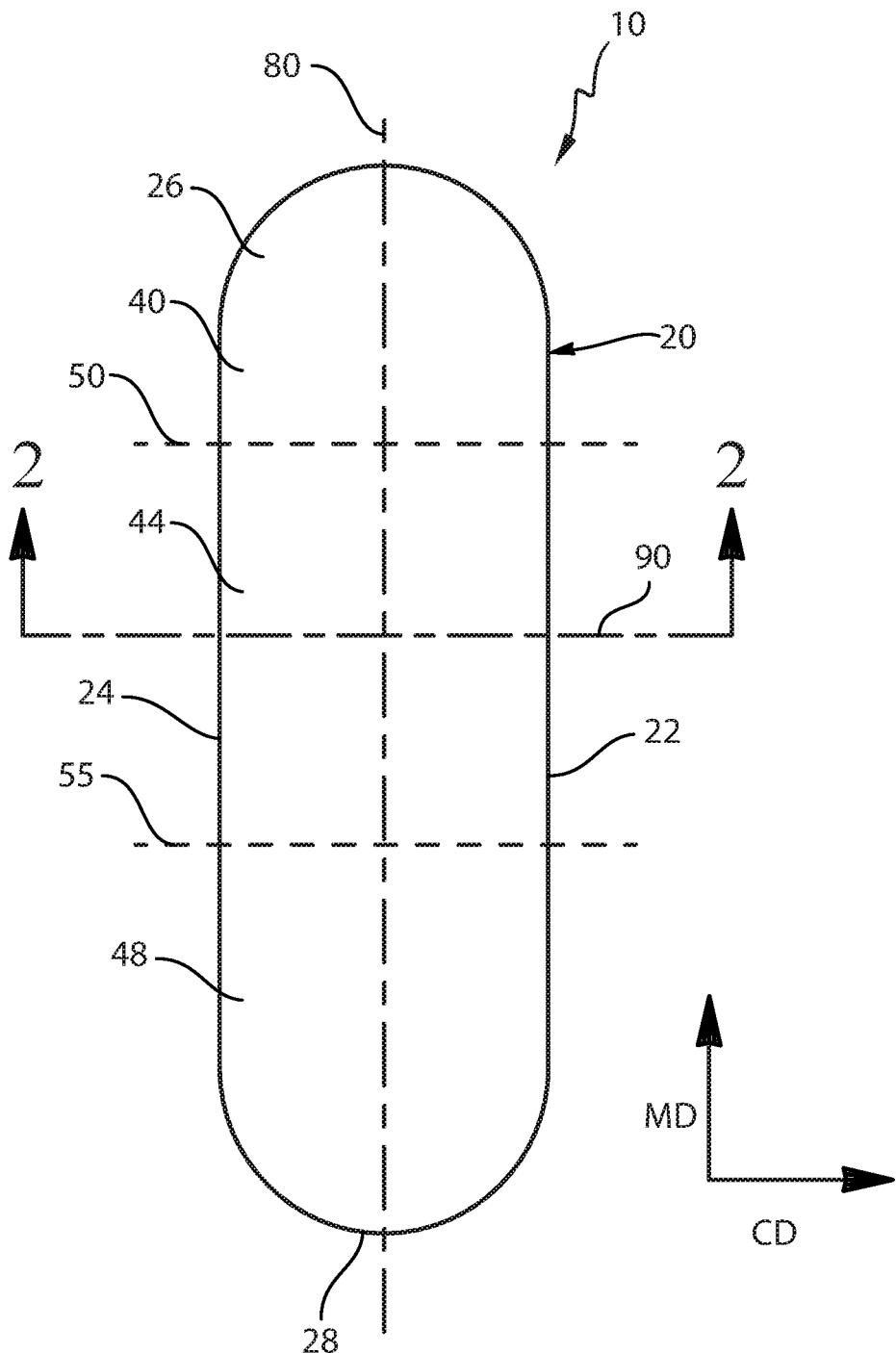
FIG. 1 is a plan view showing an exemplary embodiment of a disposable absorbent article of the present invention, which is an incontinence pad.

FIG. 1 shows an absorbent article of the present invention or more particularly an incontinence pad or sanitary napkin 10 (referred to mainly as "incontinence pad" herein) may comprise a longitudinal axis 80 and a lateral axis 90. The longitudinal axis 80 generally extends parallel to the longest dimension of the incontinence pad 10. The lateral axis 90 extends generally perpendicular to the longitudinal axis 80 and lies in the same plane as the incontinence pad 10 in a flattened state on a flat surface. The lateral axis 90 bisects the length of the incontinence pad 10 where the length is parallel to the longitudinal axis 80, and the longitudinal axis 80 bisects the width of the incontinence pad 10 where the width is parallel to the lateral axis 90. Additionally, as shown, the MD direction may be generally parallel to the longitudinal axis 80 of the incontinence pad 10, and the CD direction may be generally parallel to the lateral axis 90.

The incontinence pad 10 comprises a generally elongated oval shape. However, any suitable shape may be utilized. Some examples include hourglass (peanut), offset hourglass (one end is wider than an opposite end and a narrowed mid-section between the ends), etc. The incontinence pad 10 may be symmetric about the longitudinal axis 80 or asymmetric about the longitudinal axis 80. Similarly, the incontinence pad 10 may be symmetric about the lateral axis 90 or asymmetric about the lateral axis 90.

The incontinence pad 10 may further comprise a chassis 20 comprising a plurality of side edges 22 and 24 which extend generally parallel to the longitudinal axis 80. A pair of end edges 26 and 28 join each of the side edges 22 and 24. One end edge 26 joins the side edges 22 and 24 in the first end region 40 of the incontinence pad 10 while the other end edge 28 joins the side edges 22 and 24 in the second end region 48 of the incontinence pad 10—the second end region 48 being opposite the first end region 40. An intermediate region 44 is disposed between the first end region 40 and the second end region 48.

Figure 2:
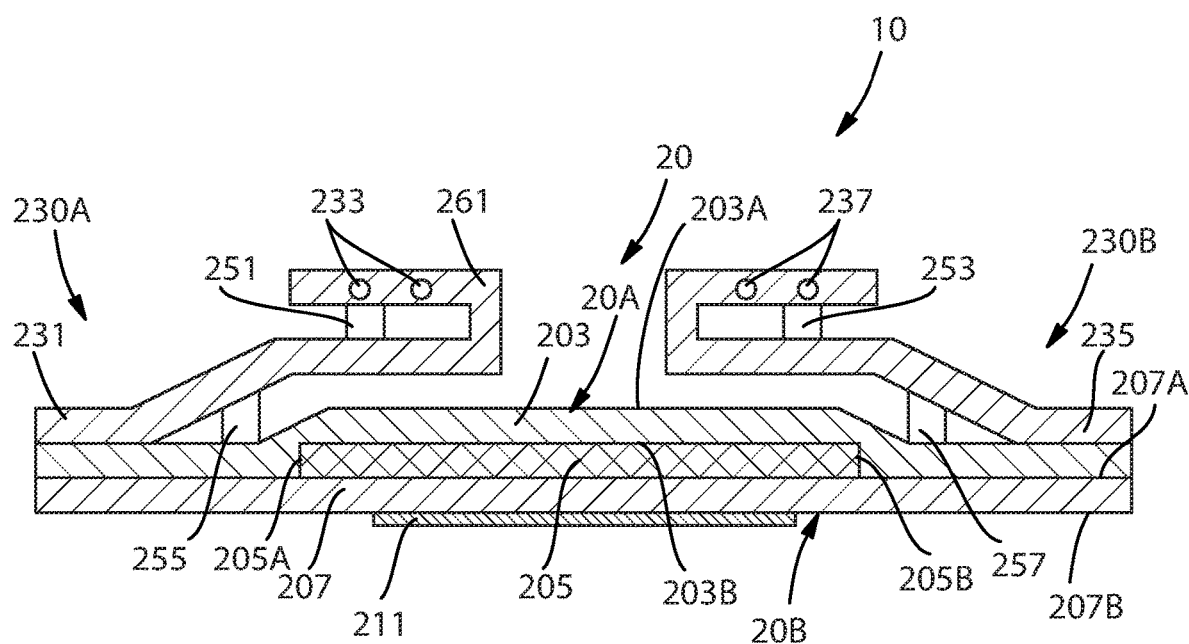
FIG. 2 is a cross-sectional view of the incontinence pad shown in FIG. 1 taken along 2-2.

The chassis 20 of FIG. 1 is shown in cross-section in FIG. 2. Among other things, the chassis 20 comprises a primary topsheet 203. This primary topsheet has a body-facing surface 203A and a garment-facing surface 203B. This chassis 20 of the pad 10 further comprises a backsheet 207 which also comprises its own body-facing surface 207A and opposing garment-facing surface 207B. These two components sandwich an absorbent core 205. In other words, the absorbent core 205 is disposed between the topsheet 203 and the backsheet 207. All three components (i.e., topsheet 203, backsheet 207, and absorbent core 205) form the chassis 20 of the pad 10. Additional layers may very well be included within this chassis 20, particularly between the topsheet 203 and the backsheet 207 but it should be noted that these layers are separate and apart from the absorbent core. Suitable additional layers may include secondary topsheets, acquisition layers, additional distribution layers over and above those which will be discussed below, and other useful layers. In the case of a secondary topsheet, it is disposed beneath the primary topsheet 203 and on the body-facing surface of the core. In certain embodiments, the secondary topsheet (also known as the "STS") has a greater length and width than the absorbent core 205.

The chassis 20 further comprises a wearer-facing surface 20A and a garment-facing surface 20B. The wearer-facing surface 20A may comprise the topsheet 203, and the garment-facing surface 20B may comprise the backsheet.

Figure 3:
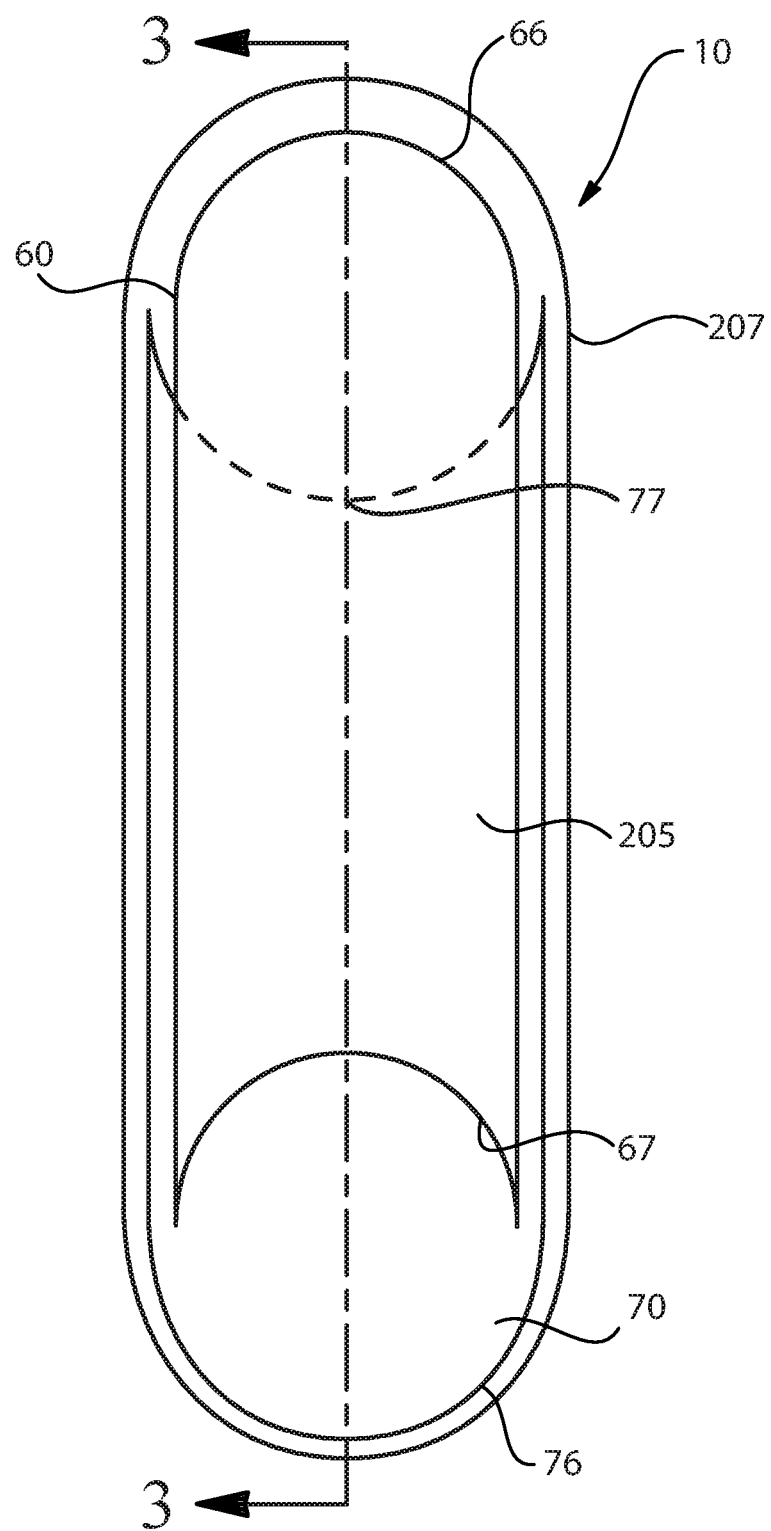
FIG. 3 is a plan view of the pad of FIG. 1 with the primary topsheet removed.
Figure 4:
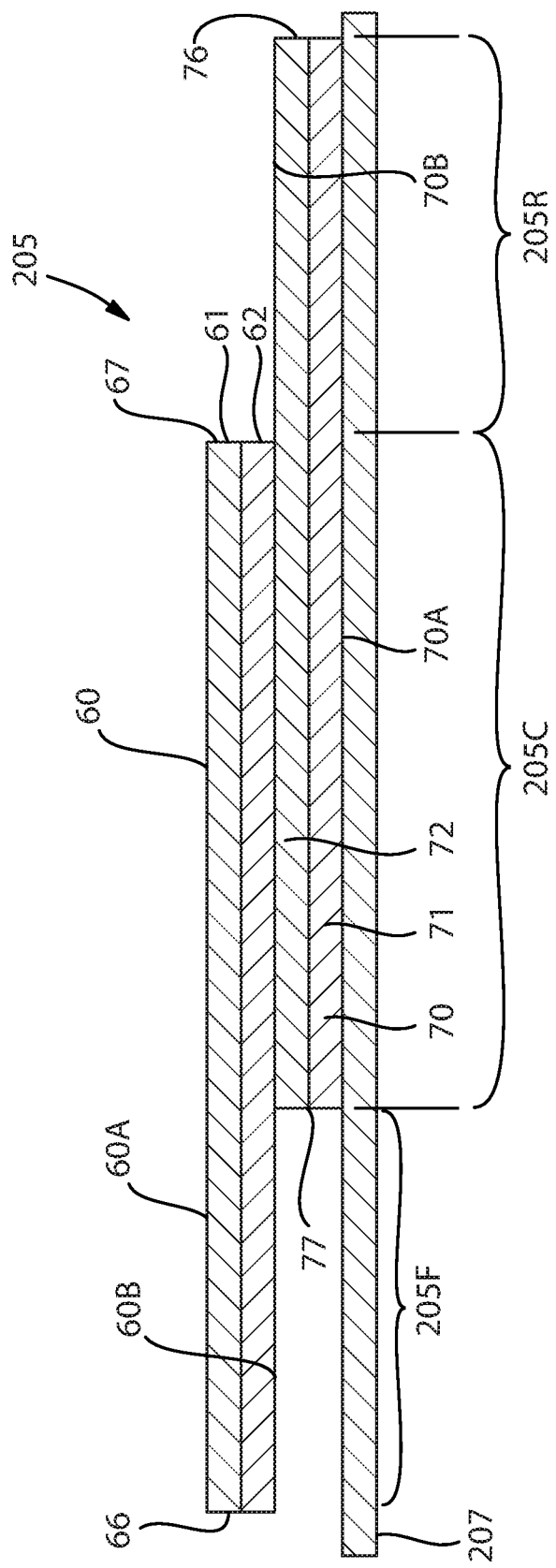
FIG. 4 is a cross-sectional view of the absorbent core of the pad of FIG. 3.

The absorbent core 205 is formed from multiple layers and is directed to quickly acquiring the bodily fluid or exudates and distributing them along a length of the core. FIG. 3 depicts the absorbent core of the present invention as it shows a plan view of the pad 10 with the primary topsheet 203 removed for viewing of the absorbent core 205 positioned above the backsheet 207. FIG. 4 shows a cross-section of this absorbent core 205 in more detail. The absorbent core 205 comprises a first laminate 60 which includes a first superabsorbent layer 61 disposed on a first distribution layer 62. The first laminate 60 has an upper surface 60A and a lower surface 60B which opposes the upper surface. Additionally, the first laminate 60 has a first end 66 and a second end 67 which opposes the first end 66. The absorbent core 205 further includes a second laminate 70 which includes a second superabsorbent layer 71 disposed on a second distribution layer 72. This second laminate 70 also has an upper surface 70A and a lower surface 70B, a first end 76, and a similar opposing second end 77. In the embodiment of FIGS. 3 and 4, the first distribution layer 62 is joined to the second distribution layer 72 in an offset manner or configuration along the length of the core. As used herein "offset" or "offset manner" means that the layers or laminates of interest are staggered and that their respective first ends or second ends are not aligned in the z-direction (i.e., the first end of one layer or laminate is not coterminous with the second end of an adjacent underlying or overlying layer or laminate) when the layers or laminates overlay one another. This offset joinder of the first and second distribution layers 62, 72 results in an overlapping and joined area of the two laminates that forms a central portion 205C of the absorbent core 205. The central portion 205C of the core is consequently bounded on each side by a front end portion and a rear end portion 205R, both of the core. In other words, the front end portion 205F and the rear end 205R portion are respectively disposed at opposing ends of the core 205. The front end portion 205F is formed from a first end 66 or second end 67 of the first laminate 60 while the rear end portion 205F of the core 205 is formed by the first end 76 or second end 77 of the second laminate 70. In the embodiment of FIG. 3, the first ends 66, 76 of the first and second laminates oppose each other and form a front end portion 205F and a rear end portion 205R of the absorbent core 205, respectively. In an alternate embodiment, the second ends 67, 77 of the first and second laminates may oppose each other and form a front end portion 205F and a rear end portion 205R of the absorbent core 205, respectively. In both instances, the first ends 66, 76 are in the form of a male connection derived from a nested cut of the first and second laminates. Similarly, the second ends 67, 77 are in the form of a female connection derived from a nested cut of the first and second laminates, respectively.

In an alternate embodiment, the first laminate 60 and the second laminate 70 may be joined to superabsorbent layer 71 instead of the second distribution layer. In this instance, the laminates are joined to one another in an offset manner as well except the first distribution layer 62 is joined to the second superabsorbent layer 71 instead of the second distribution layer.

In one embodiment, the overlapping area or region that forms the central portion 205C of the core 205 has at least one characteristic of a greater capacity, a greater void volume, or a greater thickness than the front end portion 205F and the rear end portion 205F of the absorbent core 205. This embodiment is particularly useful for providing for heightened leakage protection in the central portion where female users of such pads would typically contact the pad and release fluids.

Applicant shall now provide more detailed insight into the characteristics of the article that have been found to be desirable to provide consumers with the discretion and leak-proof benefits they seek.

Article Length

Over and above the elemental portions described herein, the overall article exhibits an article length of from about 371 mm to about 500 mm according to the Article Length Method. In certain embodiments, the article length is greater than 371 mm, 380 mm, 390 mm, and 395 mm and less than 500 mm, 490 mm, 480 mm, 470 mm, 460 mm, 450 mm, 440 mm, 430 mm, 420 mm, and 410 mm. In an embodiment, the article length is about 400 mm. The length of the disposable absorbent article is important for a variety of reasons. First, the article must be of sufficient length to cover the intended area of insult that the article is likely to experience during use. This means that to the extent a consumer expects that the fluids dispelled during the time of article wear are relatively minimal due since the product is being worn during the day time and there is easier access to toilet facilities, a shorter pad may suffice. Additionally, a shorter pad may also be more suitable during the day when the wearer's body is in a seated or standing position and the area of insult is almost orthogonal to the area of fluid expulsion, i.e., the genitalia. As a wearer's absorbency needs increase for reasons such as inaccessibility to toilet facilities, heightened inability to control urine events due to decreased mobility or weakened bladder control, it is likely desirable to increase the pad length to allow for incorporation of more absorbent material and a greater area of coverage where expelled fluids may be retained. Additionally, a disposable absorbent article that is worn at night or while a wearer is in a bed tends to be of the longest pad length. This is typically the case for since the wearer may not be able to react as quickly as required to reach the toilet facilities in a timely fashion if sleeping or laying down. Moreover, as a wearer is laying down and fluids are expelled, there is usually a tendency of the expelled fluids to creep farther along the length of the pad due to the gravitational pull on the fluid along the surface of the genital area to the gluteal area if she is laying on their back or to the groin if she is laying on their stomach. It should be noted that although article length may typically be assumed to correspond to a pad type product, it is envisioned herein that such a pad could very well be integrated into a pant product that may be worn in place of underwear.

Acquisition Time

Another important property of the disposable absorbent articles of the present invention is the speed with which they absorb expelled fluids. In order to meet the needs of the relatively high BMI consumer, it is key that she feel that her absorbency requirements are being met when she dons an incontinence product or a similar product. In reality, it is likely that many commercially available incontinence products are capable of absorbing the fluids to which they are exposed. The consumer, however, wants confidence that the product will absorb fluids quickly and do so with minimal bulk. The articles of the present invention take this concern into account. As such, pursuant to the Speed of Acquisition with Balloon Applied Pressure Method, the present articles exhibit an Acquisition Time for a load of 60 ml of less than about 39 seconds, less than about 37 seconds, less than about 35 seconds, or even less than about 30 seconds. This test method focuses on characterizing the ability of a product to absorb rather substantial gushes of fluid. The article of the present invention is focused on providing a balance of acceptable rate of fluid acquisition along with an acceptable product thickness (or even thinness) and further an ability to recover when exposed to compressive forces.

Dry Pad Thickness

In conjunction with the abovementioned properties, the articles of the present invention also exhibit a dry pad thickness of between about 5 mm to about 11 mm according to a Pad Thickness Method. As mentioned relative to the desirable acquisition time, it is important to the consumer that she be able to wear her disposable absorbent product with confidence in its absorbency performance. Almost as critical as absorbency to her is the concept of the article being discreet. This means that the consumer would like to wear the article without it being noticeable by others and without a constant reminder to herself that she is wearing it because she needs to wear it. From this perspective, it is desirable that the article be as thin as feasible. Therefore, the articles of the present invention exhibit a dry pad thickness of greater than about 5 mm, 5.5 mm, or 6 mm and less than about 11 mm, 10 mm, 9 mm, 8.5 mm, 8 mm, 7.5 mm, or 7 mm.

Energy of Recovery

From a physical property point of view, the articles of the present invention also exhibit a particular Energy of Recovery at a load of 30 ml of from about 4 mJ to about 11 mJ according to a Bunch Compression Method. In certain embodiments where the pad length is greater than about 330 mm, the Energy of Recovery is measured on a dry pad and the articles of the present invention exhibit an Energy of Recovery while dry of greater than 4.4 mJ. One of the primary concerns of wearers of incontinence is the perceived lack of protection that results when a wearer's incontinence product bunches in the crotch area during wear. This is particularly prevalent in situations where the wearer has a relatively high BMI since the product may likely be subject to heighted bunching due to the pressure of the convergence of the wearer's thighs. In order to address this concern, the present invention is focused on delivering a disposable article that not only addresses the requirements for absorbency and discretion but equally addresses the need to resist bunching as a result of compression. The resistance to bunching during wear is even more critical once the article has been insulted by fluid which is typically when articles sag and deform away from the body of the wearer due to the weight of the fluid. This resistance to bunching tends to only increase in criticality as the number of insults or gushes of fluids occur in the same article or product. Thus, it is desirable, as has been envisioned in the case of the present invention that the article exhibit sufficient resistance to bunching to accommodate multiple fluid gushes and maintain sufficient closeness to or contact with the genital area where fluid is exiting the body. This ensures that the likelihood of leaks are minimized and ultimately leads to heightened confidence of the article wearer. This resistance to bunching is characterized as an energy of recovery and is measured in conjunction with an insult of 30 ml of fluid as detailed in the Bunch Compression Method. In certain embodiments, the Energy of Recovery at a load of 30 ml according to this Bunch Compression Method is greater than about 4 ml, 4.3 ml, 4.5 ml, 5.1 mJ or 5.2 mJ and less than about 11 mJ, 10 mJ, 9 mJ, 8 mJ, 7 mJ, or 6 mJ.

The individual components of these disposable absorbent articles that are envisioned to enable and deliver these properties are detailed below.

Primary Topsheet

The primary topsheet 203 (also referred to herein "topsheet") of the chassis 20 is positioned adjacent a body-facing surface 203A of the absorbent core 205 and may be joined thereto and to the backsheet 207 by attachment methods (not shown) such as those well known in the art. Suitable attachment methods are described with respect to joining the backsheet 207 to the absorbent core 205. The topsheet 203 and the backsheet 207 may be joined directly to each other in the incontinence pad periphery and may be indirectly joined together by directly joining them to the absorbent core 205 or additional optional layers within the chassis like a secondary topsheet which spans the entire or partial area of the article. This indirect or direct joining may be accomplished by attachment methods which are well known in the art.

The absorbent article may comprise any known or otherwise effective primary topsheet, such as one which is compliant, soft feeling, and non-irritating to the wearer's skin. Suitable primary topsheet materials include a liquid pervious material that is oriented towards and contacts the body of the wearer permitting bodily discharges to rapidly penetrate through it without allowing fluid to flow back through the topsheet to the skin of the wearer. The primary topsheet, while being capable of allowing rapid transfer of fluid through it, also provides for the transfer or migration of the lotion composition onto an external or internal portion of a wearer's skin. A suitable topsheet can be made of various materials such as woven and nonwoven materials; apertured film materials including apertured formed thermoplastic films, apertured plastic films, and fiber-entangled apertured films; hydro-formed thermoplastic films; porous foams; reticulated foams; reticulated thermoplastic films; thermoplastic scrims; or combinations thereof.

Apertured film materials suitable for use as the topsheet include those apertured plastic films that are non-absorbent and pervious to body exudates and provide for minimal or no flow back of fluids through the topsheet. Nonlimiting examples of other suitable formed films, including apertured and non-apertured formed films, are more fully described in U.S. Pat. No. 3,929,135, issued to Thompson on Dec. 30, 1975; U.S. Pat. No. 4,324,246, issued to Mullane et al. on Apr. 13, 1982; U.S. Pat. No. 4,342,314, issued to Radel et al. on Aug. 3, 1982; U.S. Pat. No. 4,463,045, issued to Ahr et al. on Jul. 31, 1984; U.S. Pat. No. 5,006,394, issued to Baird on Apr. 9, 1991; U.S. Pat. No. 4,609,518, issued to Curro et al. on Sep. 2, 1986; and U.S. Pat. No. 4,629,643, issued to Curro et al. on Dec. 16, 1986. Commercially available formed filmed topsheets include those topsheet materials marketed by the Procter & Gamble Company (Cincinnati, Ohio) under the DRI-WEAVE® tradename.

Nonlimiting examples of woven and nonwoven materials suitable for use as the topsheet include fibrous materials made from natural fibers, modified natural fibers, synthetic fibers, or combinations thereof. These fibrous materials can be either hydrophilic or hydrophobic, but it is preferable that the topsheet be hydrophobic or rendered hydrophobic. As an option, portions of the topsheet can be rendered hydrophilic, by the use of any known method for making topsheets containing hydrophilic components. One such method include treating an apertured film component of a nonwoven/apertured thermoplastic formed film topsheet with a surfactant as described in U.S. Pat. No. 4,950,264, issued to Osborn on Aug. 21, 1990. Other suitable methods describing a process for treating the topsheet with a surfactant are disclosed in U.S. Pat. Nos. 4,988,344 and 4,988,345, both issued to Reising et al. on Jan. 29, 1991. The topsheet may have hydrophilic fibers, hydrophobic fibers, or combinations thereof.

A particularly suitable topsheet comprises staple length polypropylene fibers having a denier of about 1.5, such as Hercules type 151 polypropylene marketed by Hercules, Inc. of Wilmington, Del. As used herein, the term "staple length fibers" refers to those fibers having a length of at least about 15.9 mm (0.62 inches).

When the primary topsheet comprises a nonwoven fibrous material in the form of a nonwoven web, the nonwoven web may be produced by any known procedure for making nonwoven webs, nonlimiting examples of which include spunbonding, carding, wet-laid, air-laid, meltblown, needle-punching, mechanical entangling, thermo-mechanical entangling, and hydroentangling. A specific example of a suitable meltblown process is disclosed in U.S. Pat. No. 3,978,185, to Buntin et al., issued Aug. 31, 1976. The nonwoven may be compression resistant as described in U.S. Pat. No. 7,785,690 entitled "Compression Resistant Nonwovens" issued on Aug. 31, 2010. The nonwoven web may have loops as described in U.S. Pat. No. 7,838,099 entitled "Looped Nonwoven Web" issued on Nov. 23, 2010.

Other suitable nonwoven materials include low basis weight nonwovens, that is, nonwovens having a basis weight of from about 18 g/m² to about 25 g/m². An example of such a nonwoven material is commercially available under the tradename P-8 from Veratec, Incorporation, a division of the International Paper Company located in Walpole, Mass. Other nonwovens are described in U.S. Pat. Nos. 5,792,404 and 5,665,452.

The topsheet may comprise tufts as described in U.S. Pat. No. 8,728,049 entitled "Absorbent Article Having a Tufted Topsheet" issued on May 20, 2014, U.S. Pat. No. 7,553,532 entitled "Tufted Fibrous Web" issued on Jun. 30, 2009, U.S. Pat. No. 7,172,801 entitled "Tufted Laminate Web" issued on Feb. 6, 2007, or U.S. Pat. No. 8,440,286 entitled "Capped Tufted Laminate Web" issued on May 14, 2013. The primary topsheet may have an inverse textured web as described in U.S. Pat. No. 7,648,752 entitled "Inverse Textured Web" issued on Jan. 19, 2010. Tufts are also described in U.S. Pat. No. 7,410,683 entitled "Tufted Laminate Web" issued on Aug. 12, 2008.

The primary topsheet may have a pattern of discrete hair-like fibrils as described in U.S. Pat. No. 7,655,176 entitled "Method of Making a Polymeric Web Exhibiting A Soft and Silky Tactile Impression" issued on Feb. 2, 2010 or U.S. Pat. No. 7,402,723 entitled "Polymeric Web Exhibiting A Soft And Silky Tactile Impression" issued on Jul. 22, 2008.

The primary topsheet may comprise one or more structurally modified zones as described in U.S. Pat. No. 8,614,365 entitled "Absorbent Article" issued on Dec. 24, 2013. The primary topsheet may have one or more out of plane deformations as described in U.S. Pat. No. 8,704,036 entitled "Sanitary Napkin for Clean Body Benefit" issued on Apr. 22, 2014. The primary topsheet may have a masking composition as described in U.S. Pat. No. 6,025,535 entitled "Topsheet For Absorbent Articles Exhibiting Improved Masking Properties" issued on Feb. 15, 2000.

Another suitable primary topsheet or a primary topsheet combined with a secondary topsheet may be formed from a three-dimensional substrate as detailed in a U.S. provisional patent application No. 62/306,676 filed on Mar. 11, 2016 in the name of Jill M. On and entitled "A Three-Dimensional Substrate Comprising a Tissue Layer". This three-dimensional substrate has a first surface, a second surface, land areas and also comprises three-dimensional protrusions extending outward from the second surface of the three-dimensional substrate, wherein the three-dimensional protrusions are surrounded by the land areas. The substrate is a laminate comprising at least two layers in a face to face relationship, the second layer is a tissue layer facing outward from the second surface of the three-dimensional substrate, and the tissue layer comprises at least 80% pulp fibers by weight of the tissue layer.

The primary topsheet may have comprises one or more layers, for example a spunbond-meltblown-spunbond material. The primary topsheet may be apertured, may have any suitable three-dimensional features, and/or may have a plurality of embossments (e.g., a bond pattern). The topsheet may be apertured by overbonding a material and then rupturing the overbonds through ring rolling, such as disclosed in U.S. Pat. No. 5,628,097, to Benson et al., issued on May 13, 1997. Additional lateral extensibility in the chassis 20 (i.e., in the primary topsheet and/or the backsheet) may be provided in a variety of ways. For example, either the primary topsheet or backsheet may be pleated by any of many known methods. Alternatively, all or a portion of the chassis (i.e., also the primary topsheet and/or backsheet) may be made of a formed web material or a formed laminate of web materials like those described in U.S. Pat. No. 5,518,801 issued on 21 May 1996 in the name of Chappell et al. Such a formed web material includes distinct laterally extending regions in which the original material has been altered by embossing or another method of deformation to create a pattern of generally longitudinally oriented alternating ridges and valleys. The formed web material also includes laterally extending unaltered regions located between the laterally extending altered regions.

Secondary Topsheet

As noted previously, the disposable absorbent articles of the present disclosure may comprise additional layers, one of which includes a secondary topsheet. As mentioned previously, the secondary topsheet may be separate and apart from the absorbent core. Additionally, the secondary topsheet is disposed beneath the primary topsheet 203 and on the body-facing surface of the core. In some forms, the secondary topsheet may have a basis weight from about 40 gsm to about 100 gsm, from about 45 gsm to about 75 gsm, or from about 50 gsm to about 60 gsm, specifically including all values within these ranges and any ranges created thereby. In some forms, the secondary topsheet may comprise a homogeneous mix of fibers.

In other forms, the secondary topsheet may comprise a heterogeneous mix of fibers. For example, typically a plurality of carding machines feed a spunlace process. The types of fibers supplied to the cards may be homogeneously blended as mentioned above. Or in contrast, the types of fibers or the weight percentage of the fibers provided to the carding machines may be different. In such forms, where the types of fibers and/or the weight percentage of the fibers are varied to the carding machines, the resulting spunlaced structure may comprise a plurality of heterogeneous strata which are—after the spunlacing process—integral with one another.

For those forms where a secondary topsheet comprises a plurality of heterogeneous strata, an acquisition gradient may be achieved with careful selection of the fibers within each of the stratum of the secondary topsheet. For example, a first stratum—being closest in proximity to the primary topsheet—may comprise a lower amount of absorbent fiber as opposed to a stratum which is disposed further from the primary topsheet. In such forms, the first stratum may comprise from between about 20 weight percent to about 30 weight percent of absorbent fiber while an opposing stratum disposed furthest from the primary topsheet may comprise about 35 percent by weight of absorbent fiber. In such forms, the weight percentage of the stiffening fiber may stay constant among the strata or may be varied to create a stiffness gradient in the secondary topsheet in addition to the absorbency gradient. Similarly, in some forms, the resilient fibers may stay constant among the strata or may be varied to create a permeability gradient in the secondary topsheet in addition to the absorbency gradient or in addition to the stiffness gradient. Forms are contemplated where the secondary topsheets of the present disclosure comprise between 2 to 4 strata.

Some exemplary fibers that may be included in the secondary topsheet may include absorbent fibers, stiffening fibers, and resilient fibers. Forms are contemplated where at least one of the absorbent fibers, stiffening fibers, and/or resilient fibers comprise a hydrophilic coating. Suitable hydrophilic coatings are known in the art. Additionally, in some forms, the one or more of the above fibers of the secondary topsheet may comprise a staple length, e.g. about 38 mm.

Any suitable absorbent fibers may be utilized. Conventional absorbent fibers include cotton, \ rayon or regenerated cellulose. In some specific forms, the secondary topsheet may comprise viscose cellulose fibers. Due to the proximity of the secondary topsheet to the topsheet, the absorbent fibers can help to pull liquid insults from the topsheet into the absorbent core disposed beneath the secondary topsheet. In some forms, the secondary topsheet may comprise from about 20 percent to about 50 percent by weight, from about 21 percent to about 40 percent by weight, from about 25 percent to about 30 percent by weight, specifically including any values within these ranges and any ranges created thereby. In one specific form, the secondary topsheet may comprise about 25 percent by weight absorbent fibers.

It is worth noting that a higher weight percentage of absorbent fibers may be beneficial for fluid insults that are more viscous, e.g. menstrual fluid. However, the introduction of a higher weight percentage of absorbent fibers can negatively impact resiliency and stiffness of the secondary topsheet. And, too low of a weight percentage of absorbent fibers can result in a more 'wet feeling' topsheet which can create a negative impression of the product in consumers' minds. The weight percentages provided above may work well in the context of urinary fluid insults.

Any suitable size of absorbent fiber may be utilized. A suitable measure of size can be linked to linear density. In some forms, the absorbent fiber linear density may range from about 2 dtex to about 4 dtex, about 2.5 dtex to about 3.7 dtex, or from about 2.8 dtex to about 3.5 dtex, specifically reciting all values within these ranges and any ranges created thereby. In one specific form, the absorbent fiber may comprise a dtex of about 3.3.

The absorbent fibers may have any suitable shape. In some forms, a trilobal shape may be utilized. The trilobal shape can improve wicking and improve masking. Trilobal rayon is available from Kelheim Fibres and sold under the trade name Galaxy.

In addition to absorbent fibers, as mentioned previously, the secondary topsheet may also comprise stiffening fibers. Stiffening fibers may be utilized to help provide structural integrity to the secondary topsheet web material. The stiffening fibers can help increase structural integrity of the secondary topsheet in a machine direction and in a cross machine direction which facilitate web manipulation during processing of the secondary topsheet for incorporation into a disposable absorbent article. For example, the secondary topsheets of the present disclosure may be heat stiffened. The heat stiffening process can create a plurality of connection points amongst the stiffening fibers. In general, the higher the number of connection points, the stiffer the secondary topsheet. So, while the creation of a plurality of connection points is beneficial for processability, the creation of too many connection points can lead to a secondary topsheet which is uncomfortable in its respective disposable absorbent article. With that in mind, the constituent material of the stiffening fibers, the weight percentage of the stiffening fibers, and heat of processing should be carefully selected. The heat stiffening process is discussed hereafter.

With the foregoing in mind, any suitable stiffening fiber may be utilized. Some examples of suitable stiffening fibers include bi-component fibers comprising polyethylene and polyethylene terephthalate components or polyethylene terephthalate and co-polyethylene terephthalate components. The components of the bi-component fiber may be arranged in a core sheath arrangement, a side by side arrangement, an eccentric core sheath arrangement, a trilobal arrangement, or the like. In one specific example, the stiffening fibers may comprise bi-component fibers having polyethylene/polyethylene terephthalate components arranged in a concentric, core—sheath arrangement where the polyethylene is the sheath. In some forms, monocomponent fibers may be utilized. In such forms, the constituent material of the monocomponent may comprise polypropylene.

Any suitable size of stiffening fiber may be utilized. Suitable linear densities of stiffening fiber may be from about 4 dtex to about 12 dtex, from about 4.5 dtex to about 10 dtex, or from about 5 dtex to about 7 dtex, specifically reciting all values within these ranges and any ranges created thereby. In one specific form, the stiffening fibers may comprise 5.8 dtex polyethylene/polyethylene terephthalate bi-component fibers arranged in a core and concentric sheath arrangement.

Any suitable weight percentage of stiffening fibers may be utilized in the secondary topsheeet as well. However, in some forms, the secondary topsheet of the present disclosure may be heat treated (heat stiffened). The heat treatment can create connection points amongst the fibers of the secondary topsheet. So, where there is a higher percentage of stiffening fibers, more connection points may be created. The additional connection point can yield a much stiffer secondary topsheet which may negatively impact comfort. In some forms, the secondary topsheet may comprise about 20 percent to about 40 percent by weight stiffening fibers or from about 25 percent to about 35 percent by weight stiffening fibers, specifically including all values within these ranges and any ranges created thereby.

As noted previously, the secondary topsheet of the present disclosure may additionally comprise resilient fibers. The resilient fibers can help the secondary topsheet maintain its permeability. Any suitable size fiber may be utilized. In some forms, the resilient fibers can have a linear density of about 6 dtex to about 12 dtex, from about 8 dtex to about 11 dtex, or from about 9 dtex to about 10 dtex, specifically reciting all values within these ranges and any ranges created thereby. In one specific form, the resilient fibers may be comprise a linear density of about 10 dtex. In one specific example, the resilient fibers may comprise 10 dtex hollow spiral polyethylene terephthalate fibers.

It is worth noting, that if smaller fiber sizes are utilized, the resiliency of the secondary topsheet would be expected to decrease. And, with the decreased size at the same weight percentage, a higher number of fibers per gram would equate to a decrease in permeability of the secondary topsheet. Additionally, some conventional secondary topsheet may utilize superabsorbent polymer, e.g. AGM, to help drain their respective topsheets. As noted previously, AGM typically swells when absorbing fluid insults and can reduce permeability of secondary topsheets by occluding openings in the secondary topsheet. However, in general, conventional secondary topsheets have lower permeability which helps reduce the likelihood that the AGM will occlude openings of these conventional secondary topsheets upon swelling. In contrast, due to the higher permeability of the secondary topsheets of the present disclosure, AGM may not be suitable for utilization therewith without additional measures ensuring that the AGM will not greatly reduce the permeability thereof. Rather, AGM may be provided in a separate layer in an absorbent article.

Any suitable weight percentage of resilient fibers may be utilized. In some forms, the secondary topsheet of the present disclosure may comprise from about 25 percent to about 55 percent by weight resilient fibers, between 35 percent and 50 percent resilient fibers, or between 40 percent and 45 percent by weight resilient fibers, specifically including any values within these ranges and any ranges created thereby. In some specific forms, the secondary topsheet may comprise about 45 percent by weight resilient fibers. In some specific forms, the secondary topsheet may comprise about 45 percent, 10 dtex, hollow spiral polyethylene terephthalate fibers.

With regard to the heat stiffening process, any suitable temperature may be utilized. And, the suitable temperature may be impacted, in part, by the constituent chemistry of the stiffening fibers as well as by processing speed of the secondary topsheet web. In some forms, the secondary topsheet web may be heat stiffened at a temperature of 132 degrees Celsius. It is also worth noting that in order to provide a uniform stiffness property across the secondary topsheet web, any heating operation should be set up to provide uniform heating to the secondary topsheet web. Even small variations in temperature can greatly impact the tensile strength of the secondary topsheet web. For example, for two comparable secondary topsheets having a basis weight of about 50 gsm, both with the above formulations, a significant difference was created with a small temperature difference. A heat stiffening process at 135 degrees C. yielded a CD direction tensile strength for one sample that was twice the CD direction tensile strength of a sample subjected to a 132 degrees C. stiffening process. A similar result was witnessed for samples having comparable compositions and about a 70 gsm basis weight. Additionally, there was about a 1.5 times difference for the MD direction tensile strength where the sample subjected to the higher temperature, i.e. 135 degrees C., had a higher tensile strength in the MD direction.

Data is provided below in Table 1 regarding a comparison between a commercially available secondary topsheet and a secondary topsheet of the present disclosure.

TABLE 1

|  | Comparative STS Sample | Experimental STS Sample |
| --- | --- | --- |
| Basis Weight (gsm) | 75 | 50. |
| Thickness (mm) | — | 1.05 |
| Thickness Slitted (mm) | 1. | 0.80 |
| Fluid Acquisition (s) | 1.2 | 1.2 |
| Rewet (g) | 3.5 | 2 |
| Wicking MD (mm) | 25 | 20 |
| Air permeability ($m^3/m^2/min$) | 250 | 400 |
| Tensile strength MD (N) | 25 | 20 |
| Tensile strength CD (N) | 6 | 6 |
| Modulus MD (N/cm) | 50 | 50 |
| Opacity (%) | — | 43 |

The experimental sample from Table 1 was a 50 gsm basis weight secondary topsheet comprising 25% galaxy 3.3 dtex trilobal rayon available from Kelheim Fibres; 30% 5.8 detex PE/PET bicomponent, concentric—core/sheath—PE sheath; 45%, 10 dtex, 38 mm staple length, hollow spiral polyethylene terephthalate fibers.

Backsheet

The backsheet 207 of the chassis 20 may be positioned adjacent a garment-facing surface of the absorbent core 205 and may be joined thereto by attachment methods (not shown) such as those well known in the art. For example, the backsheet 207 may be secured to the absorbent core 205 by a uniform continuous layer of adhesive, a patterned layer of adhesive, or an array of separate lines, spirals, or spots of adhesive. Alternatively, the attachment methods may comprise using heat bonds, pressure bonds, ultrasonic bonds, dynamic mechanical bonds, or any other suitable attachment methods or combinations of these attachment methods as are known in the art. Forms of the present disclosure are also contemplated wherein the absorbent core 205 is not joined to the backsheet 207, the topsheet 203, or both.

The backsheet 207 may be impervious, or substantially impervious, to liquids (e.g., urine) and may be manufactured from a thin plastic film, although other flexible liquid impervious materials may also be used. As used herein, the term "flexible" refers to materials which are compliant and will readily conform to the general shape and contours of the human body. The backsheet 207 may prevent, or at least inhibit, the exudates absorbed and contained in the absorbent core 205 from wetting articles of clothing which contact the incontinence pad 10 such as undergarments. However, in some instances, the backsheet 207 may permit vapors to escape from the absorbent core 205 (i.e., is breathable) while in other instances the backsheet 207 may not permit vapors to escape (i.e., non-breathable). Thus, the backsheet 205 may comprise a polymeric film such as thermoplastic films of polyethylene or polypropylene. A suitable material for the backsheet 207 is a thermoplastic film having a thickness of from about 0.012 mm (0.5 mil) to about 0.051 mm (2.0 mils), for example. Any suitable backsheet known in the art may be utilized with the present invention.

The backsheet 207 acts as a barrier to any absorbed bodily fluids that may pass through the absorbent core 205 to the garment surface thereof with a resulting reduction in risk of staining undergarments or other clothing. Further, the barrier properties of the backsheet permit manual removal, if a wearer so desires, of the interlabial absorbent article with reduced risk of hand soiling. A preferred material is a soft, smooth, compliant, liquid and vapor pervious material that provides for softness and conformability for comfort, and is low noise producing so that movement does not cause unwanted sound.

The backsheet may comprise a wet laid fibrous assembly having a temporary wet strength resin incorporated therein as described in U.S. Pat. No. 5,885,265 (Osborn, III.) issued Mar. 23, 1999. The backsheet may further be coated with a water resistant resinous material that causes the backsheet to become impervious to bodily fluids without impairing the spreading of adhesive materials thereon.

Another suitable backsheet material is a polyethylene film having a thickness of from about 0.012 mm (0.5 mil) to about 0.051 mm (2.0 mils). The backsheet may be embossed and/or matte finished to provide a more cloth-like appearance. Further, the backsheet may permit vapors to escape from the absorbent core 42 (i.e., the backsheet is breathable) while still preventing body fluids from passing through the backsheet. A preferred microporous polyethylene film which is available from Tredegar Corporation, Virginia, USA, under Code No. XBF-1 12W.

For a stretchable but non-elastic backsheet, one material can be used is a hydrophobic, stretchable, spun laced, non-woven material having a basis weight of from about 30 to 40 g/m2, formed of polyethylene terephthalate or polypropylene fibers. This material is breathable, i.e. permeable to water vapor and other gases.

For an elastic backsheet, one material which can be used is an elastic film sold under the trade mark EXX500 by Exxon Corporation. The material of this film is formed from an elastomeric base composition consisting of a styrene block copolymer. However, this material is not breathable. Another material which can be used for an elastic backsheet is a plastic film that has been subjected to a process that provides it with elastic-like properties without attaching elastic strands to the film, and may for example comprise a formed film made in accordance with U.S. Pat. No. 4,342,314 (Radel et al) and U.S. Pat. No. 4,463,045 (Ahr et al).

Suitable breathable backsheets for use herein include all breathable backsheets known in the art. In principle there are two types of breathable backsheets, single layer breathable backsheets which are breathable and impervious to liquids and backsheets having at least two layers, which in combination provide both breathability and liquid imperviousness. Suitable single layer breathable backsheets for use herein include those described for example in GB A 2184 389, GB A 2184 390, GB A 2184 391, U.S. Pat. Nos. 4,591,523, 3,989,867, 3,156,242 and WO 97/24097.

The backsheet may have two layers: a first layer comprising a gas permeable aperture formed film layer and a second layer comprising a breathable microporous film layer as described in U.S. Pat. No. 6,462,251 (Cimini) issued Oct. 8, 2002. Suitable dual or multi-layer breathable backsheets for use herein include those exemplified in U.S. Pat. Nos. 3,881,489, 4,341,216, 4,713,068, 4,818,600, EP 203 821, EP 710 471, EP 710 472, and EP 793 952.

The backsheet may be a relatively hydrophobic 18 grams per square meter (gsm) spunbonded nonwoven web of 2 denier polypropylene fibers. The backsheet may also be a laminate as is known in the art.

The backsheet may be vapor permeable as described in U.S. Pat. No. 6,623,464 (Bewick-Sonntag) issued Sep. 23, 2003 or U.S. Pat. No. 6,664,439 (Arndt) issued Dec. 16, 2003. The backsheet can be formed from any vapor permeable material known in the art. Backsheet can be a microporous film, an apertured formed film, or other polymer film that is vapor permeable, or rendered to be vapor permeable, as is known in the art.

The backsheet may be a nonwoven web having a basis weight between about 20 gsm and about 50 gsm. In one embodiment, the backsheet is a relatively hydrophobic 23 gsm spunbonded nonwoven web of 4 denier polypropylene fibers available from Fiberweb Neuberger, under the designation F102301001. The backsheet may be coated with a non-soluble, liquid swellable material as described in U.S. Pat. No. 6,436,508 (Ciammaichella) issued Aug. 20, 2002. The backsheet has a garment-facing side and an opposite body-facing side. The garment-facing side of the backsheet comprises a non-adhesive area and an adhesive area. The adhesive area may be provided by any conventional means. Pressure sensitive adhesives have been commonly found to work well for this purpose.

Absorbent Core

The absorbent core 205 of the present invention may comprise any suitable shape including but not limited to an oval, a discorectangle, a rectangle, an asymmetric shape, and an hourglass. For example, in some forms of the present invention, the absorbent core 205 may comprise a contoured shape, e.g. narrower in the intermediate region than in the end regions. As yet another example, the absorbent core may comprise a tapered shape having a wider portion in one end region of the pad which tapers to a narrower end region in the other end region of the pad. The absorbent core 205 may comprise varying stiffness in the MD and CD.

As detailed earlier, the absorbent core 205 comprises a first laminate and a second laminate. Both are generally compressible, conformable, non-irritating to the wearer's skin, and capable of absorbing and retaining liquids such as urine and other certain body exudates including menses.

The configuration and construction of the absorbent core 205 may vary (e.g., the absorbent core 205 may have varying caliper zones, a hydrophilic gradient, a superabsorbent gradient, or lower average density and lower average basis weight acquisition zones). Further, the size and absorbent capacity of the absorbent core 205 may also be varied to accommodate a variety of wearers. However, the total absorbent capacity of the absorbent core 205 should be compatible with the design loading and the intended use of the disposable absorbent article or incontinence pad 10.

In some forms of the present invention, the absorbent core 205 may comprise a plurality of multi-functional layers that are in addition to the first and second laminates. For example, the absorbent core 205 may comprise a core wrap (not shown) useful for enveloping the first and second laminates and other optional layers. The core wrap may be formed by two nonwoven materials, substrates, laminates, films, or other materials. In a form, the core wrap may only comprise a single material, substrate, laminate, or other material wrapped at least partially around itself.

The absorbent core 205 of the present disclosure may comprise one or more adhesives, for example, to help immobilize the SAP or other absorbent materials within the first and second laminates.

Absorbent cores comprising relatively high amounts of SAP with various core designs are disclosed in U.S. Pat. No. 5,599,335 to Goldman et al., EP 1,447,066 to Busam et al., WO 95/11652 to Tanzer et al., U.S. Pat. Publ. No. 2008/0312622A1 to Hundorf et al., and WO 2012/052172 to Van Malderen. These may be used to configure the superabsorbent layers.

Additions to the core of the present disclosure are envisioned. In particular, potential additions to the current multi-laminate absorbent core are described in U.S. Pat. No. 4,610,678, entitled "High-Density Absorbent Structures" issued to Weisman et al., on Sep. 9, 1986; U.S. Pat. No. 4,673,402, entitled "Absorbent Articles With Dual-Layered Cores", issued to Weisman et al., on Jun. 16, 1987; U.S. Pat. No. 4,888,231, entitled "Absorbent Core Having A Dusting Layer", issued to Angstadt on Dec. 19, 1989; and U.S. Pat. No. 4,834,735, entitled "High Density Absorbent Members Having Lower Density and Lower Basis Weight Acquisition Zones", issued to Alemany et al., on May 30, 1989. The absorbent core may further comprise additional layers that mimic the dual core system containing an acquisition/distribution core of chemically stiffened fibers positioned over an absorbent storage core as detailed in U.S. Pat. No. 5,234,423, entitled "Absorbent Article With Elastic Waist Feature and Enhanced Absorbency" issued to Alemany et al., on Aug. 10, 1993; and in U.S. Pat. No. 5,147,345. These are useful to the extent they do not negate or conflict with the effects of the below described laminates of the absorbent core of the present invention.

Laminates

The first and second laminates 60, 70 of the absorbent core 205 have been detailed earlier but it is important to note that these laminates may have cross-direction widths that are the same as each other or different. For instance, the first laminate may have a lesser cross-direction width than said second laminate or a greater cross-direction width than said second laminate. In certain instances, the first and second laminates have machine-direction lengths that are the same while in other instances, the first and second laminates have machine-direction lengths that are different. In the latter instance, the first laminate may have a lesser machine-direction length than the second laminate or conversely the first laminate may have a greater machine-direction length than said second laminate.

The first and second laminates 60, 70 may further comprise an optional intermediate layer disposed between the respective superabsorbent layer and distribution layer. This optional intermediate layer may comprise materials detailed herein relative to the optional layers for the chassis, in general.

Additionally, although the invention requires a first and second laminate, the absorbent article or incontinence pad of the present invention may further comprise an optional laminate comprising a superabsorbent layer and a distribution layer. This optional laminate may take the form of a third, fourth, fifth, or even additional laminates. The superabsorbent layer and distribution layer may exhibit the same or different properties detailed earlier with respect to the first and second superabsorbent and distribution layers. This optional laminates may be disposed on a body-facing surface of the first laminate or second laminate or on a garment-facing surface of the first laminate or second laminate.

The first and second laminates each have a first end 66, 76 that is complementary in shape to its respective second end 67, 77. More specifically, the first end 66 of the first laminate conforms shapewise to the second end 67 of the same laminate. The same conformance applies to the first end 76 of the second laminate relative to the second end 77 of the second laminate. For instance, the first end 66 of the first laminate fits into the second end 67 of the first laminate. This conformation results from a nested cut in the laminate that provides matching or shape fitting ends. This is also the case for the second laminate's respective first 76 and second ends 77. Likewise, this feature may also be prevalent in any optional laminates that might be incorporated into the absorbent core. This nesting or nested cut feature of the laminate allows for reduced waste of trim during manufacture. It has also been found that it is possible to configure the first and second laminates in a manner that allows for their respective first ends to oppose one another when the first and second distribution layers are overlapped and joined forming an absorbent core with a central portion 205C comprising an overlapping area. A front end portion of the core 205F is formed from a first end 66, 76 of either the first laminate or the second laminate. A rear end portion of the core 205R is similarly formed from a first end 66, 76 of the other of the first laminate or the second laminate. This configuration yields an absorbent core with matching (i.e., a male connection) ends. The first end of each laminate has a male connection while the second end of each laminate has a female connection. In such instances, the male connection of the first end fits into (conforms to the shape of) the female connection of the second end of the same laminate. In another embodiment, a front end portion of the core is formed from a first end 66, 76 of either the first laminate or the second laminate while the rear end portion of the core is formed from a second end 67, 77 of the other of the first laminate or second laminate. In this instance, the second end is shaped as a female connection and therefore does not match the front end portion of the same core. In a third embodiment, the front end portion of the core is formed from a second end of either the first laminate or the second laminate. A rear end portion of the core is similarly formed from a second end of the remaining first laminate or the second laminate. This configuration yields an absorbent core with matching (i.e., a female connection) ends. It should be noted, however, that the width of the first and second laminates may be the same or different as mentioned herein. The nested cuts of the first and second ends of each of the first and second laminates have shapes selected from the group consisting of arcs, semicircles, semi-ellipses, chevrons, rectangles, sinusoids, jigsaws, and combinations thereof.

In one embodiment, in addition to the topsheet and backsheet, the core may comprise the first laminate having a first end which is complementary in shape to its respective second end and wherein said laminate includes a first superabsorbent layer disposed onto a first distribution layer and a second laminate having a first end which is complementary in shape to its respective second end and wherein said laminate includes a second distribution layer joined to a second superabsorbent layer; wherein said first laminate layer is joined to said second laminate layer in an offset manner along a length of the absorbent article wherein the absorbent core has a front end portion that is formed by the first end of the second laminate.

In terms of the method of manufacture of the laminates of the present invention, it has been found that it is preferred to form the first laminate and the second laminate from a single laminate that is slit along its machine-direction length. This method is useful only when the first and second superabsorbent layers are the same and the first and second distribution layers are the same. This sameness may be with regard to one or more of shape, basis weight, and material. The sameness of material for the distribution layer is preferred. Once the single laminate is slit to form the first and second laminates, these first and second laminates are joined. In a certain embodiment, the first and second laminates are joined at their respective distribution layers to the other in an offset manner as detailed herein and may be done so via standard mechanical, thermal, or chemical methods known to those skilled in the art.

Figure 5:
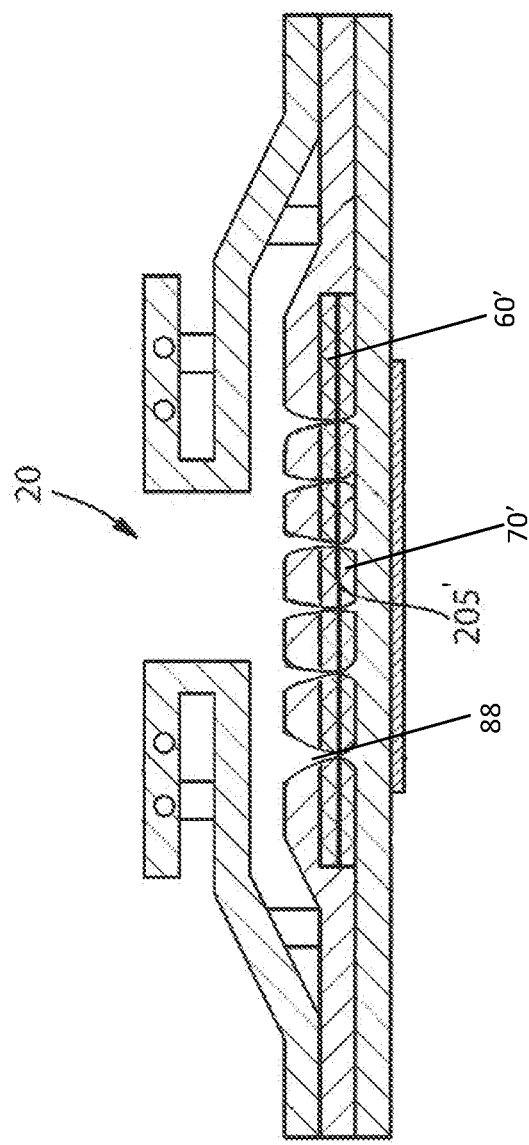
FIG. 5 is a cross-sectional view of an alternate absorbent core of the pad of FIG. 3 taken along 2-2.

In certain embodiments, the first or second laminates may include one or more recessed areas that run along the machine direction or cross direction. These recessed areas may coincide with the discontinuous patterns of one or more of a superabsorbent layer and distribution layer, whether it be of the first laminate, second laminate, or both. These recessed areas may also merely be formed by embossing of the first or second laminates. These recessed areas may alternatively be formed by slitting, cutting, ring-rolling, or otherwise providing mechanical deformation through the first and/or second laminates. Each manner of recessed area formation mentioned herein is intended to yield a recessed area that is capable of providing a point of preferential bending of the overall article. For instance, FIG. 5 shows an alternative cross-sectional view of an alternate core 205' at 2-2 where recessed areas 88 are either gaps or embossed channels in the first and second laminates 60', 70' of absorbent core 205', in the machine direction. These recessed areas 88 need not be present in both first and second laminates 60', 70' along the entirety of each of their lengths. The recessed areas 88 may be present in the machine direction only in the overlapping joinder area of the first and second laminates, 60' 70'. Alternatively, the recessed areas 88 may be present in the in the cross direction along the length of the first and second laminates, 60', 70' or only in the overlapping joinder of the two laminates. In instances like these, the laminates through which the recessed areas are effected will be prone to bending more easily. In instances where a recessed area 88 is present in only one of a first and second laminate, it is expected that there will be a preferential tendency for the pad 20 to bend at the recessed area 88. This means if the first laminate is closer to the body than the second laminate, the pad will likely bend away from the body. The opposite may be true as well in the event the second laminate 70' placed away from the body comprises a recessed area and the first laminate 60' does not. In this instance, the pad 20 may exhibit preferential tendency to bend toward the body. Depending on the overall configuration of the pad, either type of bending may be preferred in a particular instance.

Superabsorbent Layers

The first and second superabsorbent layers 61, 71 of the first and second laminates 60, 70 comprise superabsorbent polymers or absorbent gelling materials (AGM). The superabsorbent layers may comprise AGM particles or AGM fibers. In general, such AGM's have been used only for their fluid-absorbing properties. Such materials form hydrogels on contact with fluid (e.g., with urine, blood, and the like). One highly preferred type of hydrogel-forming, absorbent gelling material is based on the hydrolyzed polyacids, especially neutralized polyacrylic acid. Hydrogel-forming polymeric materials of this type are those which, upon contact with fluids (i.e., liquids) such as water or body fluids, imbibe such fluids and thereby form hydrogels. In this manner, fluid discharged into the fluid absorbent structures herein can be acquired and held. These preferred superabsorbent polymers will generally comprise substantially water-insoluble, slightly cross-linked, partially neutralized, hydrogel-forming polymer materials prepared from polymerizable, unsaturated, acid-containing monomers. In such materials, the polymeric component formed from unsaturated, acid-containing monomers may comprise the entire gelling agent or may be grafted onto other types of polymer moieties such as starch or cellulose. The hydrolyzed polyacrylic acid grafted starch materials are of this latter type. Thus the preferred superabsorbent polymers include hydrolyzed polyacrylonitrile grafted starch, hydrolyzed polyacrylate grafted starch, polyacrylates, maleic anhydride-iso-butylene copolymers and combinations thereof. Especially preferred superabsorbent polymers are the hydrolyzed polyacrylates and hydrolyzed polyacrylate grafted starch.

Whatever the nature of the polymer components of the preferred superabsorbent polymers, such materials will in general be slightly cross-linked. Cross-linking serves to render these preferred hydrogel-forming absorbent materials substantially water-insoluble, and cross-linking also in part determines the gel volume and extractable polymer characteristics of the hydrogels formed therefrom. Suitable cross-linking agents are well known in the art and include, for example: (1) compounds having at least two polymerizable double bonds; (2) compounds having at least one polymerizable double bond and at least one functional group reactive with the acid-containing monomer material; (3) compounds having at least two functional groups reactive with the acid-containing monomer material; and (4) polyvalent metal compounds which can form ionic cross-linkages. Preferred cross-linking agents are the di- or polyesters of unsaturated mono- or polycarboxylic acids with polyols, the bisacrylamides and the di- or triallyl amines. Especially preferred cross-linking agents are N,N'-methylenebisacrylamide, trimethylol propane triacrylate and triallyl amine. The cross-linking agent will generally comprise from about 0.001 mole percent to about 5 mole percent of the preferred materials. More preferably, the cross-linking agent will comprise from about 0.01 mole percent to about 3 mole percent of the absorbent gelling materials used herein.

The preferred, slightly cross-linked, hydrogel-forming absorbent gelling materials will generally be employed in their partially neutralized form. For purposes described herein, such materials are considered partially neutralized when at least about 25 mole percent, 50 mole percent, or even 75 mole percent, of monomers used to form the polymer are acid group-containing monomers which have been neutralized with a salt-forming cation. Suitable salt-forming cations include alkali metal, ammonium, substituted ammonium and amines. This percentage of the total monomers utilized which are neutralized acid group-containing monomers is referred to as the "degree of neutralization." Typically, commercial superabsorbent polymers have a degree of neutralization somewhat less than about 90%.

The preferred superabsorbent polymers used herein are those which have a relatively high capacity for imbibing fluids encountered in the fluid absorbent articles; this capacity can be quantified by referencing the "gel volume" of said superabsorbent polymers. Gel volume can be defined in terms of the amount of synthetic urine absorbed by any given fluid absorbent gelling agent buffer and is specified as grams of synthetic urine per gram of gelling agent.

Gel volume in synthetic urine can be determined by forming a suspension of about 0.1-0.2 parts of dried fluid absorbent gelling material to be tested with about 20 parts of synthetic urine. This suspension is maintained at ambient temperature under gentle stirring for about 1 hour so that swelling equilibrium is attained. The gel volume (grams of synthetic urine per gram of fluid absorbent gelling material) is then calculated from the weight fraction of the gelling agent in the suspension and the ratio of the liquid volume excluded from the formed hydrogel to the total volume of the suspension. The preferred superabsorbent polymers useful in this invention will have a gel volume of from about 20 to 70 grams, more preferably from about 30 to 60 grams, of synthetic urine per gram of absorbent gelling material.

The superabsorbent polymers hereinbefore described are typically used in the form of discrete particles. Such superabsorbent polymers can be of any desired shape, e.g., spherical or semi-spherical, cubic, rod-like polyhedral, etc. Shapes having a large greatest dimension/smallest dimension ratio, like needles and flakes, are also contemplated for use herein. Agglomerates of fluid absorbent gelling material particles may also be used.

The size of the fluid absorbent gelling material particles may vary over a wide range. For reasons of industrial hygiene, average particle sizes smaller than about 30 microns are less desirable. Particles having a smallest dimension larger than about 2 mm may also cause a feeling of grittiness in the absorbent article, which is undesirable from a consumer aesthetics standpoint. Furthermore, rate of fluid absorption can be affected by particle size. Larger particles have very much reduced rates of absorption. Fluid absorbent gelling material particles preferably have a particle size of from about 30 microns to about 2 mm for substantially all of the particles. "Particle Size" as used herein means the weighted average of the smallest dimension of the individual particles.

These layers are preferably substantially free of airfelt and are thus distinct from mixed layers that may include airfelt. As used herein, "substantially free of airfelt" means less than 5%, 3%, 1%, or even 0.5% of airfelt. In a preferred case, there will be no measurable airfelt in the superabsorbent layers. In the case of the first superabsorbent layer, it is preferably disposed onto the first distribution layer discontinuously. As used herein "discontinuously" or "in a discontinuous pattern" means that the superabsorbent polymers are applied onto the first distribution layer in a pattern of disconnected shaped areas. These areas of superabsorbent polymers or areas free of superabsorbent polymer may include, but are not limited to linear strips, non-linear strips, circles, rectangles, triangles, waves, mesh, and combinations thereof. The first superabsorbent layer like the second superabsorbent layer may, however, be disposed onto its respective distribution layer in a continuous pattern. As used herein "continuous pattern" or "continuously" means that the material is deposited and or secured to a superabsorbent carrier material and/or the adjacent distribution layer in an uninterrupted manner such that there is rather full coverage of the distribution layer by the superabsorbent polymer.

In certain embodiments, the first and second superabsorbent layers may comprise superabsorbent polymers that are the same. In other embodiments, the first and second superabsorbent layers may comprise superabsorbent polymers that are different from one another. This is may be in addition to the different deposition patterns that are discussed above.

The superabsorbent layers are disposed having a thickness of 0.2 mm, 0.3 mm, 0.4 mm, or 0.5 mm to 1 mm, 1.2 mm, 1.4 mm, 1.8 mm, or 2 mm. The first and second superabsorbent layers may have the same or different cross-direction widths as applied to their respective distribution layers. For instance, the cross-direction widths of the first and second superabsorbent layers may be from 20 mm, 25 mm, 30 mm, 35 mm, or 40 mm to 50 mm, 60 mm, 65 mm, 70 mm, 80 mm, or 90 mm. Alternatively, in embodiments where the widths of the first and second superabsorbent layers differ from one another in the cross-direction width, the first superabsorbent layer may have a lesser cross-direction width than the second superabsorbent layer. In particular, the first superabsorbent layer may have a cross-direction width that is less than about 95%, 90%, 80%, 70%, or even 60% of the width of the second superabsorbent layer.

In certain embodiments, the one or both of the first and second superabsorbent layers span greater than greater than about 50%, 60%, 70%, 80%, 90%, or even 95% of the cross-direction width of a superabsorbent carrier layer and/or the respective adjoining first or second distribution layer.

Like the optional layers that may be included in the chassis, the absorbent core may also comprise similar optional layers. They may be webs selected from the group consisting of a fibrous structure, an airlaid web, a wet laid web, a high loft nonwoven, a needlepunched web, a hydroentangled web, a fiber tow, a woven web, a knitted web, a flocked web, a spunbond web, a layered spunbond/melt blown web, a carded fiber web, a coform web of cellulose fiber and melt blown fibers, a coform web of staple fibers and melt blown fibers, and layered webs that are layered combinations thereof.

These optional layers of the core and of the chassis may comprise materials such as creped cellulose wadding, fluffed cellulose fibers, airfelt, and textile fibers. The materials of the optional layers may also be fibers such as, for example, synthetic fibers, thermoplastic particulates or fibers, tricomponent fibers, and bicomponent fibers such as, for example, sheath/core fibers having the following polymer combinations: polyethylene/polypropylene, polyethylvinyl acetate/polypropylene, polyethylene/polyester, polypropylene/polyester, copolyester/polyester, and the like. The optional layers may be any combination of the materials listed above and/or a plurality of the materials listed above, alone or in combination.

The materials of the optional layers may be hydrophobic or hydrophilic depending on their placement within the chassis.

The materials of the optional layers may comprise constituent fibers comprising polymers such as polyethylene, polypropylene, polyester, and blends thereof. The fibers may be spunbound fibers. The fibers may be meltblown fibers. The fibers may comprise cellulose, rayon, cotton, or other natural materials or blends of polymer and natural materials. The fibers may also comprise a superabsorbent material such as polyacrylate or any combination of suitable materials. The fibers may be monocomponent, bicomponent, and/or biconstituent, non-round (e.g., capillary channel fibers), and may have major cross-sectional dimensions (e.g., diameter for round fibers) ranging from 0.1-500 microns. The constituent fibers of the nonwoven precursor web may also be a mixture of different fiber types, differing in such features as chemistry (e.g. polyethylene and polypropylene), components (mono- and bi-), denier (micro denier and >20 denier), shape (i.e., capillary and round) and the like. The constituent fibers may range from about 0.1 denier to about 100 denier.

The optional layers may include thermoplastic particulates or fibers. The materials, and in particular thermoplastic fibers, may be made from a variety of thermoplastic polymers including polyolefins such as polyethylene (e.g., PULPEX™) and polypropylene, polyesters, copolyesters, and copolymers of any of the foregoing.

Depending upon the desired characteristics, suitable thermoplastic materials include hydrophobic fibers that have been made hydrophilic, such as surfactant-treated or silica-treated thermoplastic fibers derived from, for example, polyolefins such as polyethylene or polypropylene, polyacrylics, polyamides, polystyrenes, and the like. The surface of the hydrophobic thermoplastic fiber may be rendered hydrophilic by treatment with a surfactant, such as a nonionic or anionic surfactant, e.g., by spraying the fiber with a surfactant, by dipping the fiber into a surfactant or by including the surfactant as part of the polymer melt in producing the thermoplastic fiber. Upon melting and resolidification, the surfactant will tend to remain at the surfaces of the thermoplastic fiber. Suitable surfactants include nonionic surfactants such as Brij 76 manufactured by ICI Americas, Inc. of Wilmington, Del., and various surfactants sold under the Pegosperse™ by Glyco Chemical, Inc. of Greenwich, Conn. Besides nonionic surfactants, anionic surfactants may also be used. These surfactants may be applied to the thermoplastic fibers at levels of, for example, from about 0.2 to about 1 g/cm$^2$ of thermoplastic fiber.

Suitable thermoplastic fibers may be made from a single polymer (monocomponent fibers), or may be made from more than one polymer (e.g., bicomponent fibers). The polymer comprising the sheath often melts at a different, typically lower, temperature than the polymer comprising the core. As a result, these bicomponent fibers provide thermal bonding due to melting of the sheath polymer, while retaining the desirable strength characteristics of the core polymer.

Suitable bicomponent fibers for use in the present invention may include sheath/core fibers having the following polymer combinations: polyethylene/polypropylene, polyethylvinyl acetate/polypropylene, polyethylene/polyester, polypropylene/polyester, copolyester/polyester, and the like. Particularly suitable bicomponent thermoplastic fibers for use herein are those having a polypropylene or polyester core, and a lower melting copolyester, polyethylvinyl acetate or polyethylene sheath (e.g., DANAKLON™, CELBOND™, or CHISSO™ bicomponent fibers). These bicomponent fibers may be concentric or eccentric. As used herein, the terms "concentric" and "eccentric" refer to whether the sheath has a thickness that is even, or uneven, through the cross-sectional area of the bicomponent fiber. Eccentric bicomponent fibers may be desirable in providing more compressive strength at lower fiber thicknesses. Suitable bicomponent fibers for use herein may be either uncrimped (i.e., unbent) or crimped (i.e., bent). Bicomponent fibers may be crimped by typical textile means such as, for example, a stuffer box method or the gear crimp method to achieve a predominantly two-dimensional or "flat" crimp.

The length of bicomponent fibers may vary depending upon the particular properties desired for the fibers and the web formation process. Typically, in an airlaid web, these thermoplastic fibers have a length from about 2 mm to about 12 mm long such as, for example, from about 2.5 mm to about 7.5 mm long, and from about 3.0 mm to about 6.0 mm long. Nonwoven fibers may be between 5 mm long and 75 mm long, such as, for example, 10 mm long, 15 mm long, 20 mm long, 25 mm long, 30 mm long, 35 mm long, 40 mm long, 45 mm long, 50 mm long, 55 mm long, 60 mm long, 65 mm long, or 70 mm long. The properties-of these thermoplastic fibers may also be adjusted by varying the diameter (caliper) of the fibers. The diameter of these thermoplastic fibers is typically defined in terms of either denier (grams per 9000 meters) or decitex (grams per 10,000 meters). Suitable bicomponent thermoplastic fibers as used in an airlaid making machine may have a decitex in the range from about 1.0 to about 20 such as, for example, from about 1.4 to about 10, and from about 1.7 to about 7 decitex.

The compressive modulus of these thermoplastic materials, and especially that of the thermoplastic fibers, may also be important. The compressive modulus of thermoplastic fibers is affected not only by their length and diameter, but also by the composition and properties of the polymer or polymers from which they are made, the shape and configuration of the fibers (e.g., concentric or eccentric, crimped or uncrimped), and like factors. Differences in the compressive modulus of these thermoplastic fibers may be used to alter the properties, and especially the density characteristics, of the respective thermally bonded fibrous matrix.

The optional layers may also include synthetic fibers that typically do not function as binder fibers but alter the mechanical properties of the fibrous webs. Synthetic fibers include cellulose acetate, polyvinyl fluoride, polyvinylidene chloride, acrylics (such as Orlon), polyvinyl acetate, non-soluble polyvinyl alcohol, polyethylene, polypropylene, polyamides (such as nylon), polyesters, bicomponent fibers, tricomponent fibers, mixtures thereof and the like. These might include, for example, polyester fibers such as polyethylene terephthalate (e.g., DACRON™, and KODEL™), high melting crimped polyester fibers (e.g., KODEL™ 431 made by Eastman Chemical Co.) hydrophilic nylon (HYDROFIL™), and the like. Suitable fibers may also hydrophilized hydrophobic fibers, such as surfactant-treated or silica-treated thermoplastic fibers derived from, for example, polyolefins such as polyethylene or polypropylene, polyacrylics, polyamides, polystyrenes, polyurethanes and the like. In the case of nonbonding thermoplastic fibers, their length may vary depending upon the particular properties desired for these fibers. Typically they have a length from about 0.3 to 7.5 cm, such as, for example from about 0.9 to about 1.5 cm. Suitable nonbonding thermoplastic fibers may have a decitex in the range of about 1.5 to about 35 decitex, such as, for example, from about 14 to about 20 decitex.

Distribution Layers

The first and second distribution layers are useful for wicking bodily fluids away from the skin of a wearer to facilitate comfort of continued wear after a release. In an embodiment, the first and second distribution layers of the first and second laminates not only face one another but are joined in an offset manner to form part of the core. The distribution layers comprise one or more of cellulose and commuted wood pulp. This may be in the form of airlaid. The airlaid may be chemically or thermally bonded. In particular, the airlaid may be multi bonded airlaid (MBAL). In this instance, the distribution layer may further comprise a fibrous thermoplastic adhesive material at least partially bonding the airlaid to itself and adjacent distribution layers, superabsorbent layers, or other additional (optional) layers. It should be noted that the same materials that are suitable for the optional layers of the chassis are envisioned as suitable for use in the distribution layers. The basis weight for each of the first and second distribution layers range from 80 gsm, 80 gsm, 100 gsm, 110 gsm, 120 gsm, or 130 gsm to 140 gsm, 150 gsm, 160 gsm, 180 gsm, 200 gsm, 220 gsm, or 240 gsm. A preferred basis weight is 135 gsm for each of the distribution layers of the first and second laminates.

Barrier Cuffs

The incontinence pad 10 may further comprise a first barrier cuff 230A and a second barrier cuff 230B and fastening adhesive 211 disposed on the garment-facing surface 20B of the chassis 20. As shown, the fastening adhesive 211 may not extend out laterally to the same extent as the absorbent core 205. As such, constructions where pad curl is reduced would be beneficial.

The first barrier cuff 230A and the second barrier cuff 230B may be attached to the chassis 20 in any suitable location. For example, as shown, the first barrier cuff 230A and the second barrier cuff 230B may be attached to a wearer-facing surface 20A of the chassis 20. As shown, the first barrier cuff 230A and the second barrier cuff 230B are attached to the primary topsheet 203. In some forms, the first barrier cuff 230A and the second barrier cuff 230B may be attached to a garment-facing surface 20B of the chassis 20. For example, the first barrier cuff 230A and the second barrier cuff 230B may be attached to the backsheet 207. Some examples of other suitable barrier cuffs are described in U.S. Pat. Nos. 4,695,278; 4,704,115; 4,795,454; 4,909,803; U.S. Patent Application Publication No. 2009/0312730.

As shown, in some forms, the first barrier cuff 230A comprises a first cover 231 and a first elastic member 233. The second barrier cuff 230B comprises a second cover 235 and a second elastic member 237. As shown, the first cover 231 may fully enclose the first elastic member 233. Similarly, the second cover 235 may fully enclose the second elastic member 237.

While the first barrier cuff 230A and the second barrier cuff 230B are shown as discrete elements which are attached to the chassis 20, any suitable configuration may be utilized. For example, the first cover 231 and/or the second cover 235 may comprise a portion of the primary topsheet 203 and/or a portion of the backsheet 207. In such forms, the first barrier cuff 230A and/or the second barrier cuff 230B may be integrally formed with the chassis 20. A form where the first barrier cuff 230A and the second barrier cuff 230B are integrally formed with the chassis 20 is shown in FIG. 2 and discussed hereafter.

Referring to FIG. 2, the first elastic member 233 and the second elastic member 237 may be attached to the first cover 231 and the second cover 235, respectively, by any suitable means. In one example, the first elastic member may be adhesively attached to the first cover 231. Similarly, the second elastic member 237 may be adhesively attached to the second cover 235. For example, as shown, first adhesive portions 251 and 253 may attach the elastic members 233 and 237 to their respective covers 231 and 235. Similarly, second adhesive portions 255 and 257 may attach their respective covers 231 and 235 to the primary topsheet 203. As described below, the first elastic member 233 and the second elastic member 237 may be attached in only a portion the first cover 231 and second cover 235, respectively. Additional forms are contemplated where the first elastic member 233 and/or the second elastic member 237 are attached to the chassis 20 in conjunction with or independently from their respective covers 231 and 235.

Referring to FIG. 2, the elastic members 233 and 237 may be disposed laterally inboard of side edges 205A and 205B of the absorbent core 205. In other forms, the elastic members 233 and 237 may be disposed laterally outboard of the side edges 205A and 205B of the absorbent core 205. Still in other forms, the elastic members 233 and 237 may be disposed laterally inboard of the side edges 205A and 205B of the absorbent core 205 in the first end region 40 and the second end region 48 but laterally outboard of side edges 205A and 205B of the absorbent core 205 in the intermediate region 44. Additional forms are contemplated where the elastic members 233 and 237 are disposed laterally inboard of the side edges 205A and 205B of the absorbent core 205 in the first end region 40 but are disposed outboard of the side edges 205A and 205B of the absorbent core 205 in the intermediate region 44 and/or the second end region 48.

The elastic members comprised by the barrier cuffs can be glued in, in various glue lengths using various glues and glue amounts and placements. Placement of the glue is yet another variable which should be considered especially when designed with the core flexibility in mind. Gluing of the elastic members and the covers create anchor points on the pad.

The covers of the barrier cuffs of the present invention can be made of varying types of nonwovens of different MD and CD flexibility. The cover can be bonded to the topsheet of the absorbent article, such as, for example, by a slot coated stripe of adhesive, glue beads, ultrasonic sealing, or other suitable bonding agents. In certain forms of the present invention, the cover can be bonded to the backsheet at the side edges 22 and 24 (see FIG. 1) of the pad, such as, for example, using a crimp or other suitable bonding agents, such as, for example, adhesive.

Elastic members may comprise any suitable elastic material. Some suitable examples include Spandex™ or other similar polyurethanes, natural or synthetic rubber, styrene block copolymers, metallocene polyolefins, Lycra™, or any other suitable elastomer materials known in the art. Preferably the elastic member is durable for ease of processing and for during the use of the article and exhibits excellent elasticity (recovery after strain) even under strains as high as 400%.

Additionally, the elastic members of the present disclosure may comprise any suitable dtex. In other forms, the elastic members may comprise a dtex of 680 or less. In some forms, the elastic members may have a dtex between 680 and 470, specifically including all numbers within the range and any ranges created thereby.

Minimum spacing between the first barrier cuff 230A and the second barrier cuff 230B may be largely driven by female anatomy. However, tradeoffs can occur where the barrier cuffs (and their respective elastic members) are disposed too far outboard of the absorbent core 205 and too far inboard of the absorbent core 205. As such, spacing between the most distal elastic members of their respective barrier cuffs should be carefully selected. Starting from the narrowest width, spacing between the most distal elastic members of the first barrier cuff 230A and the second barrier cuff 230B should be large enough to allow sufficient access to the absorbent core 205 during use while also taking into account the forces which will be applied to the pad. If too narrow, access to a portion of the absorbent core 205 could be obstructed which could lead to leakage despite the barrier cuffs 230A and 230B. In some forms of the present invention, minimum spacing between the elastic member of the first barrier cuff 230A and the elastic member of the second barrier cuff 230B which are most distal to one another may be at least 20 mm. Any suitable spacing may be utilized. For example, in some forms of the present invention, the spacing may be greater than or equal to about 20 mm, greater than about 30 mm, greater than about 33 mm, greater than about 35 mm, greater than about 40 mm, greater than about 45 mm, greater than about 50 mm, greater than about 54 mm, greater than about 60 mm, greater than about 65 mm, less than or equal to about 70 mm, or less than about 65 mm, or less than about 60 mm, less than about 55 mm, less than about 50 mm, less than about 45 mm, less than about 40 mm, less than about 35 mm, less than about 30 mm, less than about 25 mm, specifically including any values within these ranges or any ranges created thereby.

Fold Lines

Yet another factor that contributes to fit is the folds or fold lines of the pad. Pads generally contain one or more folds in order to make the pad more consumer friendly and easy to transport and store. Additionally, folding the pad can reduce the likelihood of elastic creep during storage. However, these fold lines can act as bending points upon which elastomeric forces can act to deform the shape of the pad. And, similar to the anchor points discussed above, anchor points disposed too far beyond a fold line can be problematic. Anchor points disposed too far beyond a fold line can increase the torque lever arm acting on the pad in the MD direction causing pad curl and/or the pad to fold back into the folded state.

Referring back to FIG. 1, incontinence pad 10 may further comprise a first fold line 50 and a second fold line 55. The first fold line 50 can define a boundary between the first end region 40 and the intermediate region 44. The second fold line 55 can define a boundary between the second end region 48 and the intermediate region 44. The first end region 40 can be defined by the end edge 26, the first fold line 50, and a portion of the side edges 22 and 24 disposed between the end edge 26 and the first fold line 50. The intermediate area 44 can be by the first fold line 50, the second fold line 55, and a portion of the side edges 22 and 24 disposed between the first fold line 50 and second fold line 55. The second end region 48 is defined by the second fold line 55, end edge 28, and a portion of the side edges 22 and 24 disposed between the end edge 28 and the second fold line 55. The fold lines 50 and 55 can be parallel and can be co-linear (on average) with the folds which are created via the packaging process for the incontinence pad 10.

In some forms, the first fold line 50 and second fold line 55, may be configured such that the fold lines 50 and 55 dissect the pad into thirds. In other forms, the first fold line 50 may be offset toward the end edge 28, and the second fold line 55 may be offset toward the end edge 28. In such forms, this can allow the second end region 48 to be tucked between the intermediate region 44 and the first end region 40 when the pad is in the folded configuration.

Additional Features

In some forms of the present invention, the incontinence pads or sanitary napkins may comprise wings. Wings can provide additional leakage protection for the incontinence pad and can help secure the pad to the underwear of the user. Any suitable wing configuration known in the art may be utilized.

All the components can be adhered together with adhesives, including hot melt adhesives, as is known in the art. The adhesive can be Findlay H2128 UN or Savare PM 17 and can be applied using a Dynafiber HTW system.

Per FIG. 2, during use, the pad can be held in place by any support or attachment suitable for such purposes. In certain forms of the present invention, the pad is placed in the user's undergarment or panty and secured thereto by the fastening adhesive 211. The fastening adhesive 211 secures the pad in the crotch portion of the user's panty. A portion or all of the garment-facing surface 20B of the chassis 20 is coated with fastening adhesive 211. Any adhesive or glue suitable for such purposes can be used for the fastening adhesive 211 herein, such as, for example, using pressure-sensitive adhesive. Suitable adhesives include, for example, Century A-305-IV manufactured by the Century Adhesives Corporation of Columbus, Ohio; and Instant Lock 34-2823 manufactured by the National Starch and Chemical Company of Bridgewater, N.J. Suitable adhesive fasteners are also described in U.S. Pat. No. 4,917,697. Before the absorbent article is placed in use, the pressure-sensitive adhesive is typically covered with a removable release liner in order to keep the adhesive from drying out or adhering to a surface other than the crotch portion of the panty prior to use. Suitable release liners are also described in U.S. Pat. Nos. 4,917,697 and 4,556,146. Any commercially available release liners commonly used for such purposes can be utilized herein. Non-limiting examples of suitable release liners are BL30MG-A Silox E1/0 and BL30MG-A Silox 4P/O both of which are manufactured by the Akrosil Corporation of Menasha, Wis. The pad can be used by removing the release liner and thereafter placing the absorbent article in a panty so that the adhesive contacts the panty. The adhesive maintains the absorbent article in its position within the panty during use. The release liner can also be a wrapper that can individually package the pad.

Again, although the majority of discussion herein is around incontinence pads and sanitary napkins, it is envisioned that this invention is also useful for taped diapers, training pants which pull on, adult incontinence diapers and pants, and replaceable pads for incontinence and menses collection that might be inserted and removed after use in a disposable or durable panty or underpant.

Test Methods

Article Length Method

The overall length of an absorbent article is measured as the distance between a front leading edge of a pad and a rear leading edge of a pad, along the longitudinal centerline. Measurements are made using a calibrated steel metal ruler traceable to NIST, or equivalent. Test samples are conditioned at 23° C.±2 C.° and 50%±2% relative humidity for 2 hours prior to testing and all testing is performed under these same environmental conditions.

Remove the test sample from its wrapper and if present, remove the release paper to expose the panty fastening adhesive (PFA). Apply talc powder to the PFA on the back sheet to mitigate tackiness. Suspend the article vertically by its front leading edge. Attach a 500 g±1 g weight to the rear leading edge allowing the article to hang freely. After 30 sec measure the length of the article along the longitudinal centerline of the article to the nearest 1 mm and record as the Article Length (AL). In like fashion, repeat for a total of at least four replicate test samples. Calculate the arithmetic mean and report to the nearest 1 mm.

Pad Thickness Method

The thickness of an absorbent article is measured as the distance between a reference platform on which the absorbent article rests and a pressure foot that exerts a specified amount of pressure onto the article over a specified amount of time. Pad thickness can be measured as single product stack height and caliper of individual unwrapped pads. All measurements are performed in a laboratory maintained at 23° C.±2 C.° and 50%±2% relative humidity.

Pad thickness is measured with a manually-operated micrometer equipped with a pressure foot capable of exerting a steady pressure of 0.88 kPa onto the test sample. The manually-operated micrometer is a dead-weight type instrument with readings accurate to 0.001 mm. A suitable instrument is Mitutoyo Series 543 ID-C Digimatic, available from VWR International, or equivalent. The pressure foot is a flat ground circular movable face with a diameter of 40 mm. The test sample is supported by a horizontal flat reference platform that is larger than and parallel to the surface of the pressure foot. The system is calibrated and operated per the manufacturer's instructions.

Test samples are removed from their outermost packaging (e.g., polybag) and conditioned in a room maintained at 23°

C.±2 C.° and 50%±2% relative humidity for at least 2 hours prior to testing. To measure single product stack height, thickness measurements are made on pads that remain folded inside any wrapper that is present. The test location is defined as the longitudinal and lateral midpoint of the test sample in its wrapper. Zero the micrometer against the horizontal flat reference platform. Place the test sample on the platform with the test location centered below the pressure foot. Orient the test sample so that any exposed or fastened edge of the wrapper faces the platform, not the pressure foot. Gently lower the pressure foot with a descent rate of 0.8 mm±0.1 mm per second until the full pressure is exerted onto the test sample. Wait 5 seconds and then record the thickness of the test sample to the nearest 0.01 mm. In like fashion, repeat for a total of at least four replicate test samples. Calculate the arithmetic mean for the Single Product Stack Height and report to the nearest 0.01 mm.

To measure the caliper of the individual unwrapped pad, remove the test sample from its wrapper. If folded, gently unfold it and smooth out any wrinkles. If present, remove the release paper to expose the panty fastening adhesive (PFA). Apply talc powder to the PFA on the back sheet to mitigate tackiness. The test location is defined as the longitudinal and lateral midpoint of the test sample's absorbent core. Proceed with the thickness measurement as previously stated, orienting the topsheet side of the test sample towards the pressure foot. In like fashion, repeat for a total of at least four replicate test samples. Calculate the arithmetic mean for the Pad Thickness and report to the nearest 0.01 mm.

Speed of Acquisition with Balloon Applied Pressure Method & Rewet Method

The SABAP (Speed of Acquisition with Balloon Applied Pressure) test method is designed to measure the speed at which a known volume of 0.9% saline solution is absorbed into an absorbent article which is compressed at 1.7 kPa. Time needed to absorb the dose is recorded. Subsequent to the acquisition test, PACORM (Post Acquisition Collagen Rewet Method) is performed. The test comprises measuring the mass of fluid expressed from the article under pressure after loading by the SABAP protocol. Collagen sheets are used as the rewet substrate. A suitable collagen is Naturin Coffi collagen sheets (available from Viscofan USA Inc., 50 Country Court, Montgomery, Ala. 36105, USA) or equivalent. Upon receipt, the collagen sheets are stored at about 23° C.±2 C.° and about 50%±2% relative humidity. All testing is performed in a room also maintained at about 23° C.±2 C.° and about 50%±2% relative humidity.

Figure 6:
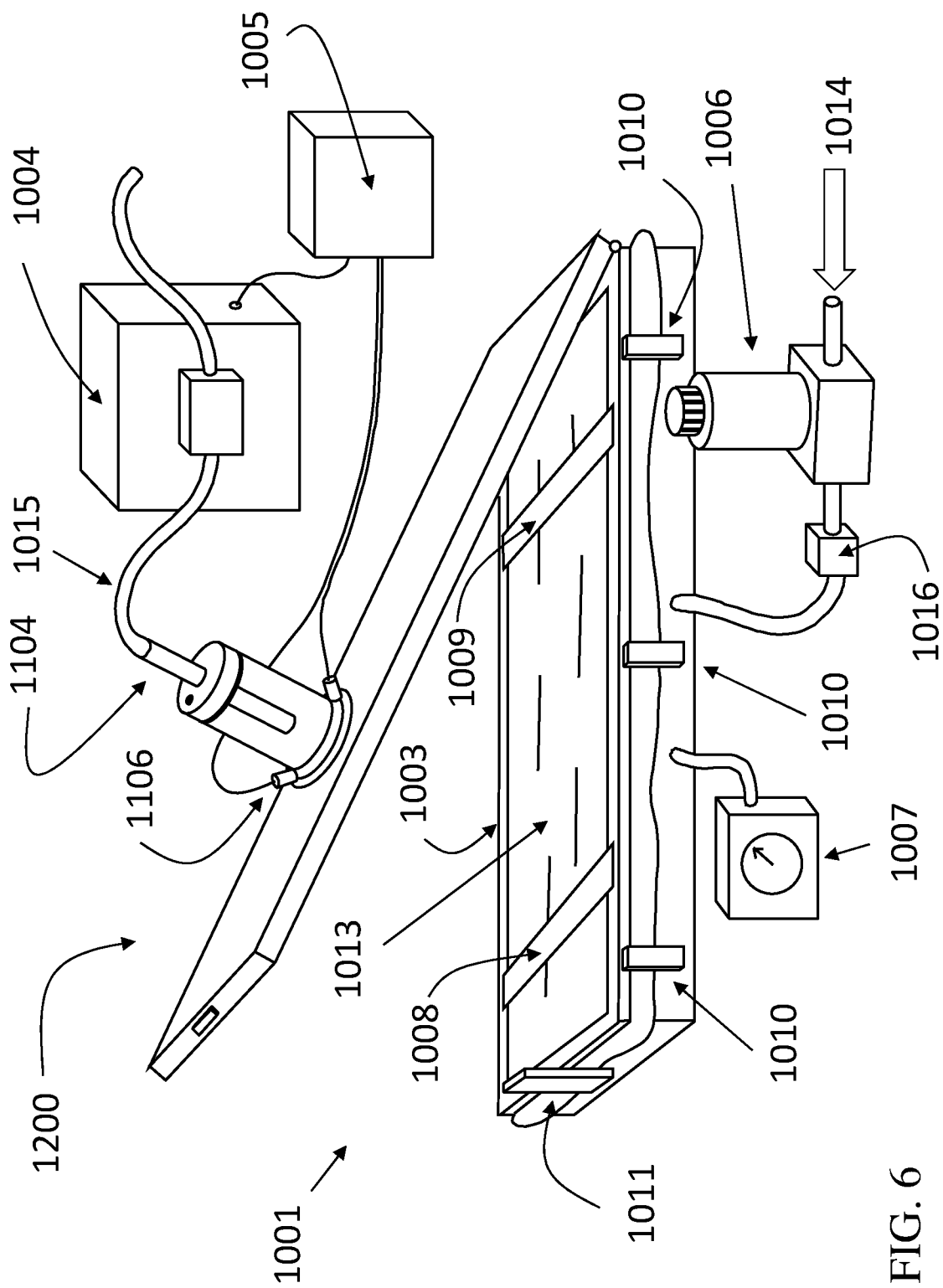
FIG. 6 is a perspective view of a SABAP apparatus useful for the SABAP method described herein.
Figure 7:
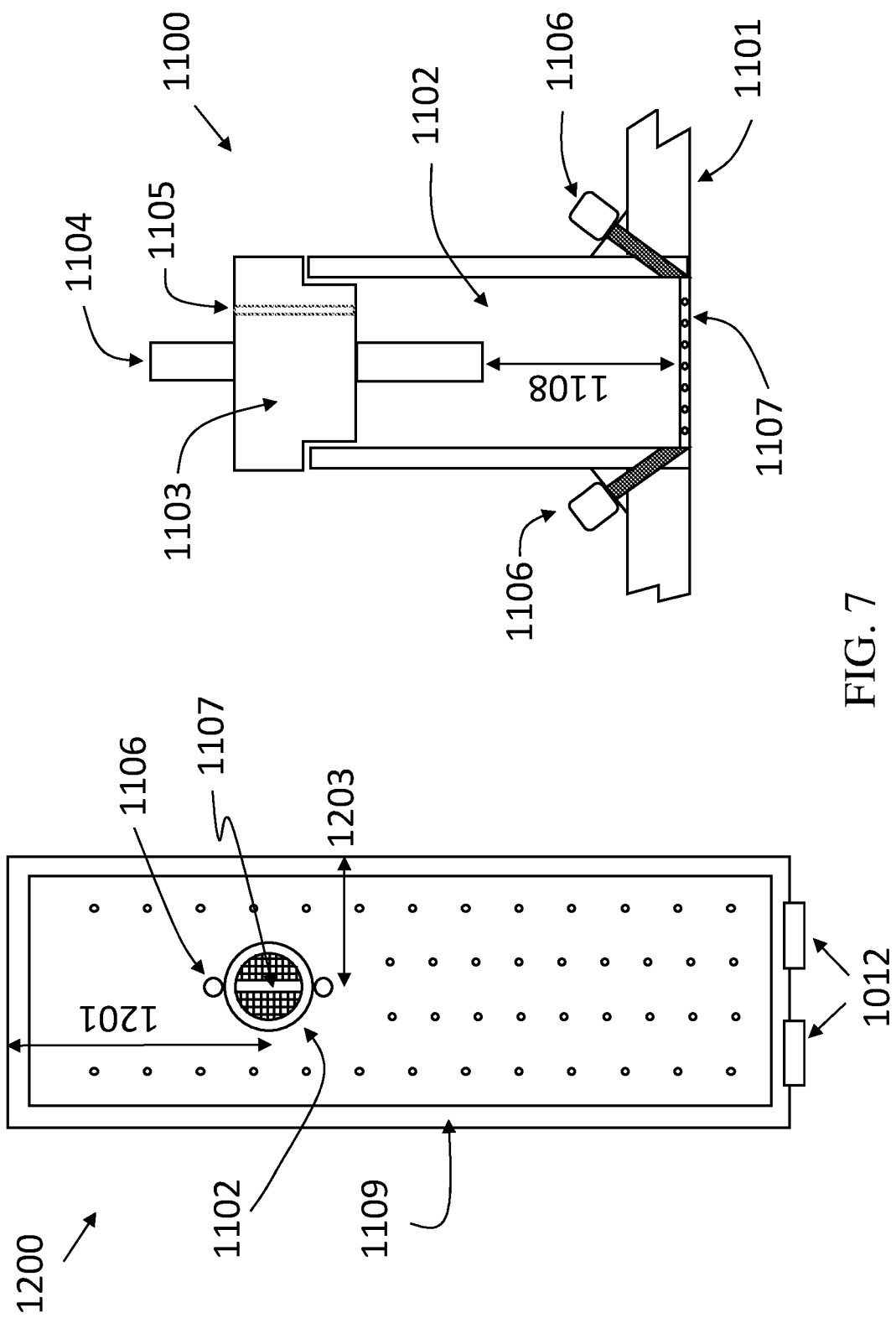
FIG. 7 is a side view of a deposition assembly and bottom view of top plate assembly of the SABAP apparatus of FIG. 6.

The SABAP apparatus is depicted in FIG. 6 and FIG. 7. It consists of a bladder assembly 1001 and a top plate assembly 1200 which includes the deposition assembly 1100. A controller 1005 is used to 1) monitor the impedance across the electrodes 1106, recording the time interval 0.9% saline solution is in the cylinder 1102, 2) interface with the liquid pump 1004 to start/stop dispensing, and 3) time intervals between dosing. The controller is capable of recording time events to ±0.01 sec. A house air supply 1014 is connected to the pressure regulator 1006 capable of delivering air at a suitable flow/pressure to maintain 1.7 kPa in the bladder assembly. A liquid pump 1004 (Ismatec MCP-Z gear pump, available from Cole Palmer, Vernon Hills, Ill. or equivalent) capable of delivering a flow of 2-120 mL at a rate of 2-20 mL/s is attached to the steel tube 1104 of the deposition assembly 1100 via Tygon® tubing 1015.

The bladder assembly 1001 is constructed of 12.7 mm Plexiglas® with an overall dimension of 80 cm long by 30 cm wide by 5 cm tall. A manometer 1007 to measure the pressure inside the assembly and a pressure gauge 1006 to regulate the introduction of air into the assembly are installed through two holes through the right side. The bladder 1013 is assembled by draping a 50 mm by 100 mm piece of silicone film, (thickness 0.02", Shore A durometer value of 20, available as Part #86435K85 from McMaster-Carr, Cleveland, Ohio) over the top of the box with enough slack that the latex touches the bottom of the box at its center point. An aluminum frame 1003 with a flange is fitted over the top of the latex and secured in place using mechanical clamps 1010. When in place the assembly should be leak free at a pressure of 3.45 kPa. A front 1008 and back 1009 sample support 5 cm by 30 cm by 1 mm are used to anchor the sample. The article is attached to the top surface of the sample supports by either adhesive tape or mechanical "hook" fasteners. These supports can be adjusted along the length of the aluminum frame 1003 via a simple pin and hole system to accommodate different size absorbent articles and to correctly align their loading point.

The top plate assembly 1200 is constructed of an 80 cm by 30 cm piece of 12.7 mm Plexiglas® reinforced with an aluminum frame 1109 to enhance rigidity. The deposition assembly 1100 is centered 30 cm (1201) from the front of the plate assembly and 15 cm (1203) from either side. The deposition assembly is constructed of a 50.8 mm O.D. Plexiglas® cylinder 1102 with a 38.1 mm I.D. The cylinder is 100 mm tall and is inserted through the top plate 1101 and flush with the bottom of the plate 1101. Two electrodes 1106 are inserted though the top plate and cylinder and exit flush with the inner wall of the cylinder immediately above the cylinders bottom surface. A nylon screen 1107 cut into two semicircles are affixed flush with the bottom of the cylinder such that the sample cannot swell into the cylinder. The cylinder is topped with a loose-fitting nylon cap 1103. The cap has a 6.35 mm O.D. steel tube 1104 inserted through its center. When the cap is in place, the bottom of the tube ends 20 mm above (1108) the screen 1107. The cap also has an air hole 1105 to ensure negative pressure does not impede the absorption speed. In addition, the top plate has forty-four (44) 3.2 mm diameter holes drilled through it distributed as shown in FIG. 7. The holes are intended to prevent air from being trapped under the top plate as the bladder is inflated but not to allow fluid to escape. The top plate assembly 1200 is connected to the bladder assembly 1001 via two hinges 1012. During use the top assembly is closed onto the bladder assembly and locked into place using a mechanical clamp 1011.

The PACORM equipment consist of a Plexiglas® disk 60.0 mm in diameter and 20 mm thick and a confining weight that rests upon it. The mass of the disk and confining weight combined is 2000 g±2 g, equivalent to 6.9 kPa of pressure. Collagen is die cut into 90.0 mm circles and stacks of four (4) assembled for use during rewet testing. Measure and record the mass of the dry collagen stack and record to the nearest 0.0001 g.

Samples are conditioned at 23° C.±2 C.° and about 50%±2% relative humidity for two hours prior to testing. The article is first prepared by excising any inner or outer leg cuffs, waist caps, elastic ears or side panels if present, taking care not to disturb the top sheet that resides above the article's core region. Place the article flat onto a lab bench and identifying the intersection of the longitudinal and lateral centerlines of the article.

Attach the front end of the article to the top surface of the front sample plate 1008 by either adhesive tape or mechanical "hook" fasteners with the top sheet facing upward. The placement is such that just the chassis and not the absorptive core overlays the plate. The sample plate 1008 is attached to the aluminum frame 1003 such that the article's absorbent core will be centered longitudinally and laterally within the cylinder 1102 when the top plate assembly has been closed. The back end of the article is secured to the back sample plate 1009 by either adhesive tape or mechanical "hook" fasteners, once again ensuring that only the chassis and not the absorptive core overlays the plate. The back sample plate 1009 is then attached to the aluminum frame 1003 such that the article is taunt but not stretched. The top plate assembly is closed and fastened, and the bladder is inflated to 1.7 kPa.

A 0.9% w/v saline solution is prepared by weighing 9.0 g±0.05 g of NaCl into a weigh boat, transferring it into a 1 L volumetric flask and diluting to volume with de-ionized water. The pump 1004 is primed then calibrated to deliver each size dependent volume and flow rate as defined in Table 2.

TABLE 2

Size Dependent Volumes and Flow Rates for Acquisition Testing

| Article Length (mm) | Volume (mL) | Rate (mL/sec) |
|---|---|---|
| 250-329 | 20.0 | 5 |
| 330-370 | 40.0 | 10 |
| >370 | 60.0 | 15 |

Volume and flow rate must be within ±2% of target. The cap 1103 is placed into the cylinder 1102. The controller 1005 is started, which in turn delivers the prescribed dose of 0.9% saline solution. If the fluid leaks out of or around the product (i.e., is not absorbed into the article) then the test is aborted. Also, if any acquisition time exceeds 1200 sec, the test is aborted. Acquisition times are recorded by the controller to the nearest 0.01 sec.

Five minutes after the test is complete (i.e., the dose has been absorbed), the pressure relief valve 1016 is opened to deflate the bladder and the sample article removed from the bladder system for PACORM (Post Acquisition Collagen Rewet Method) evaluation.

Within 30 sec, place the specimen flat on a bench top, place a pre-weighed stack of collagen centered at the longitudinal and lateral midpoint of the article's absorbent core, place a Plexiglas® disk centered onto the collagen stack, and gently place confining weight onto the disk. Wait for 30.0 sec±0.5 sec and remove the weight. Immediately measure the mass of the wet collagen and record to the nearest 0.0001 g. Calculate the rewet value as the difference between the wet and dry weight of the stack and record to the nearest 0.0001 g.

In like fashion, run a total of at least five (5) replicates for each article to be evaluated. Calculate and report the Acquisition Time as the arithmetic mean to the nearest 0.01 seconds. Calculate the Rewet for the at least five replicates as the arithmetic mean to the nearest 0.0001 g.

Bunch Compression Test Method

Bunched Compression of a sample is measured on a constant rate of extension tensile tester (a suitable instrument is the MTS Alliance using Testworks 4.0 software, as available from MTS systems Corp., Eden Prairie, Minn., or equivalent) using a load cell for which the forces measured are within 10% to 90% of the limit of the cell. All testing is performed in a room controlled at 23° C.±3 C.° and 50%±2% relative humidity. The test can be performed wet or dry.

Figure 8:
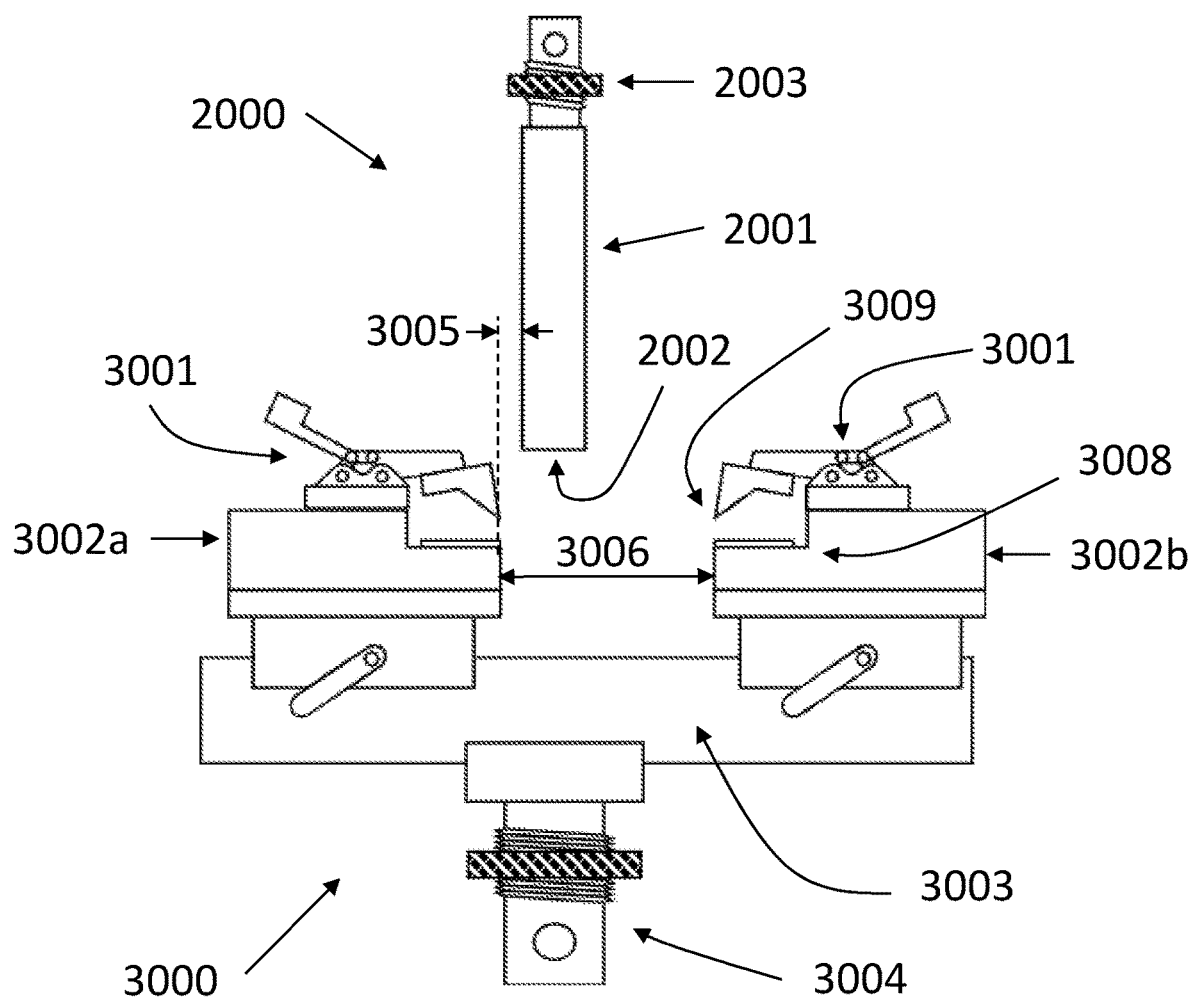
FIG. 8 is side view of an apparatus or tensile tester for use in a Bunch Compression Method of the present invention.

In FIG. 8, the bottom stationary fixture 3000 consists of two matching sample clamps 3001 each 100 mm wide each mounted on its own movable platform 3002a, 3002b. The clamp has a "knife edge" 3009 that is 110 mm long, which clamps against a 1 mm thick hard rubber face 3008. When closed, the clamps are flush with the interior side of its respective platform. The clamps are aligned such that they hold an un-bunched specimen horizontal and orthogonal to the pull axis of the tensile tester. The platforms are mounted on a rail 3003 which allows them to be moved horizontally left to right and locked into position. The rail has an adapter 3004 compatible with the mount of the tensile tester capable of securing the platform horizontally and orthogonal to the pull axis of the tensile tester. The upper fixture 2000 is a cylindrical plunger 2001 having an overall length of 70 mm with a diameter of 25.0 mm. The contact surface 2002 is flat with no curvature. The plunger 2001 has an adapter 2003 compatible with the mount on the load cell capable of securing the plunger orthogonal to the pull axis of the tensile tester.

Samples are conditioned at 23° C.±3 C.° and 50%±2% relative humidity for at least 2 hours before testing. When testing a whole article, remove the release paper from any panty fastening adhesive on the garment facing side of the article. Lightly apply talc powder to the adhesive to mitigate any tackiness. If there are cuffs, excise them with scissors, taking care not to disturb the top sheet of the product. Place the article, body facing surface up, on a bench. On the article identify the intersection of the longitudinal midline and the lateral midline. Using a rectangular cutting die, cut a specimen 100 mm in the longitudinal direction by 80 mm in the lateral direction, centered at the intersection of the midlines. When testing just the absorbent body of an article, place the absorbent body on a bench and orient as it will be integrated into an article, i.e., identify the body facing surface and the lateral and longitudinal axis. Using a rectangular cutting die, cut a specimen 100 mm in the longitudinal direction by 80 mm in the lateral direction, centered at the intersection of midlines. The specimen can be analyzed both wet and dry. The dry specimen requires no further preparation. The wet specimens are dosed with 0.9% w/v saline solution (i.e., 9.0 g of NaCl diluted to 1 L deionized water). The volume of liquid added to the specimen is determined by the overall length of the pad being tested, according to Table 3 below.

TABLE 3

| Article Length (mm) | Volume of Dose (mL) |
|---|---|
| 250-329 | 10.00 ± 0.01 |
| 330-370 | 20.00 ± 0.01 |
| >370 | 30.00 ± 0.01 |

The dose is added using a calibrated Eppendorf-type pipettor, spreading the fluid over the complete body facing surface of the specimen within a period of approximately 3 sec. The wet specimen is tested 10.0 min±0.1 min after the dose is applied.

Program the tensile tester to zero the load cell, then lower the upper fixture at 2.00 mm/sec until the contact surface of the plunger touches the specimen and 0.02 N is read at the load cell. Zero the crosshead. Program the system to lower the crosshead 15.00 mm at 2.00 mm/sec then immediately raise the crosshead 15.00 mm at 2.00 mm/sec. This cycle is repeated for a total of five cycles, with no delay between cycles. Data is collected at 100 Hz during all compression/decompression cycles.

Figure 9A:
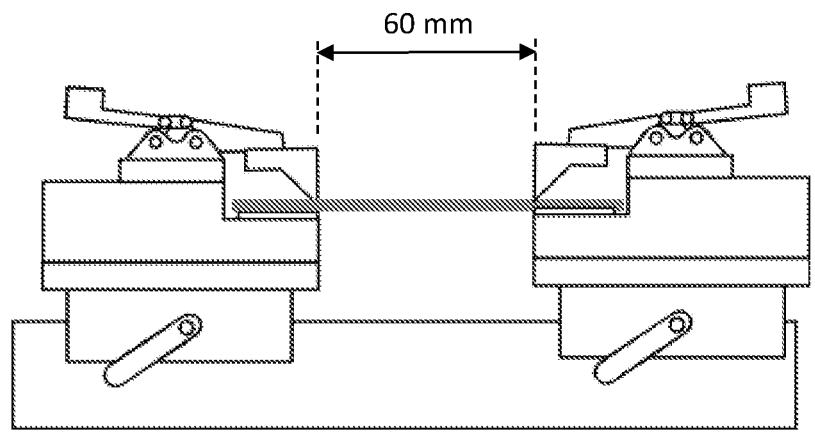
FIG. 9a is a side view of the tensile tester of FIG. 8 upon initial placement of a specimen.
Figure 9B:
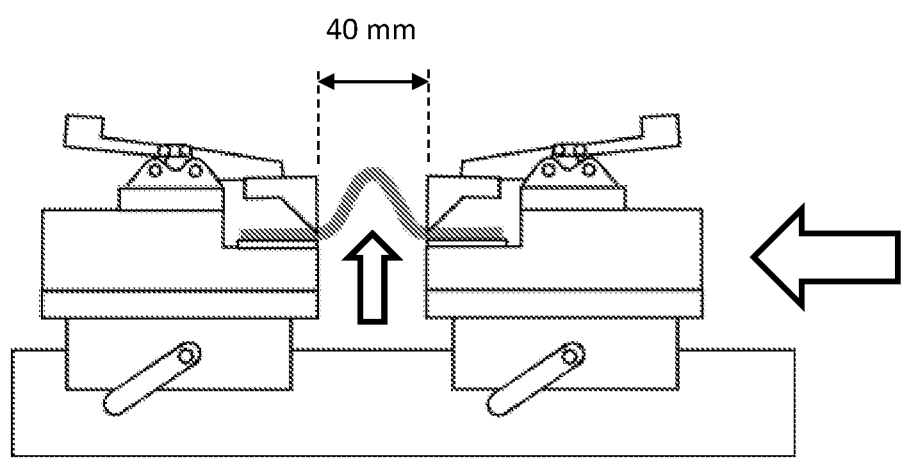
FIG. 9b is a side view of the tensile tester of FIG. 9 once the specimen has been compressed.

Position the left platform 3002a 2.5 mm from the side of the upper plunger (distance 3005). Lock the left platform into place. This platform 3002a will remain stationary throughout the experiment. Align the right platform 3002b 60.0 mm from the stationary clamp (distance 3006). Raise the upper probe 2001 such that it will not interfere with loading the specimen. Open both clamps. Referring to FIG. 9a, place the specimen with its longitudinal edges (i.e., the 100 mm long edges) within the clamps. With the specimen laterally centered, securely fasten both edges. Referring to FIG. 9b, move the right platform 3002b toward the stationary platform 3002a a distance 20.0 mm. Allow the specimen to bow upward as the movable platform is positioned. Manually lower the probe 2001 until the bottom surface is approximately 1 cm above the top of the bowed specimen.

Figure 10A:
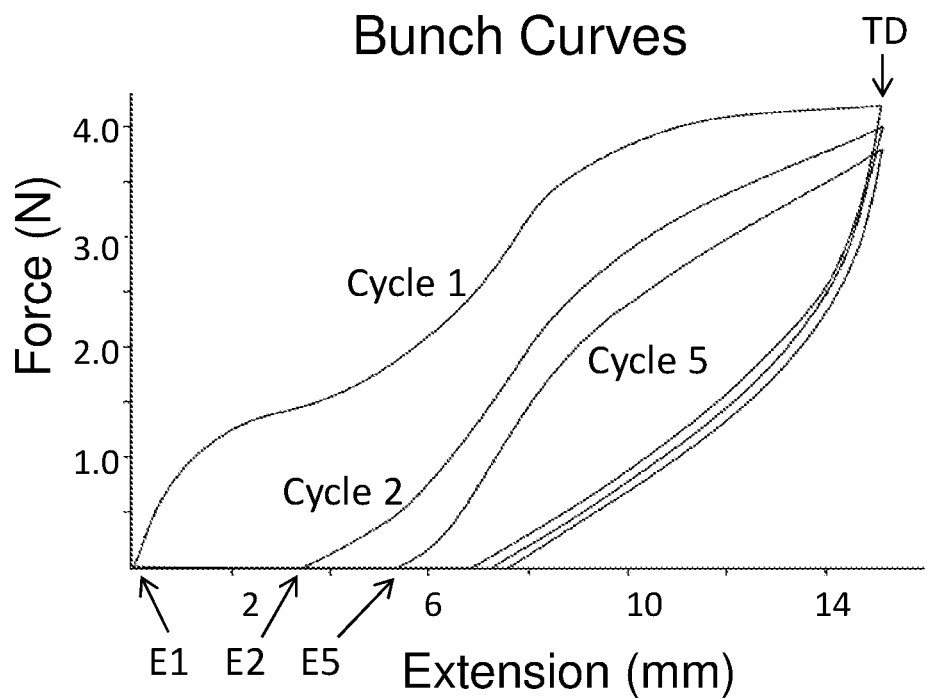
FIG. 10a is an exemplary graph of bunch compression curves where force versus displacement of samples tested is shown pursuant to a Bunch Compression Method as detailed herein
Figure 10B:
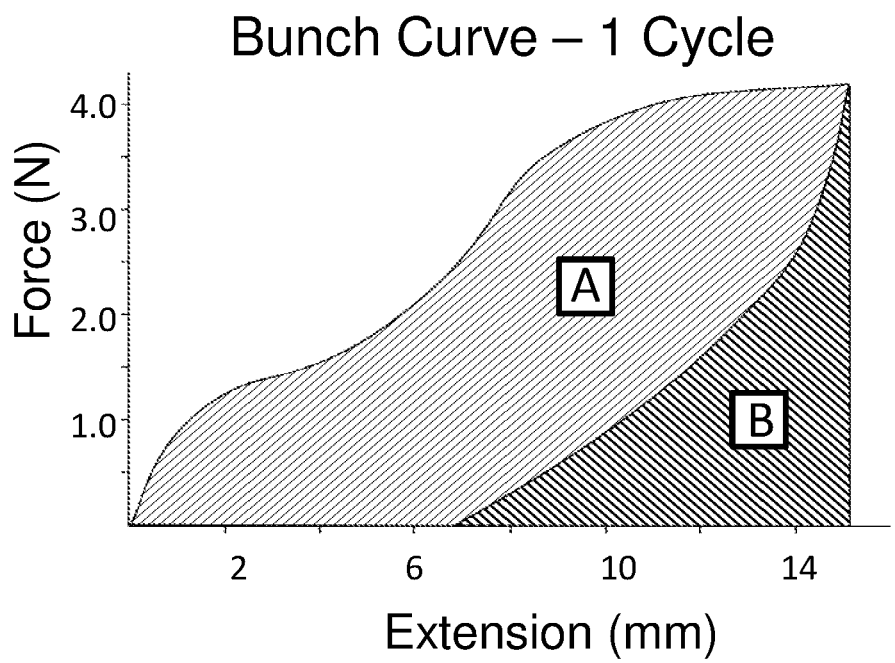
FIG. 10b is a bunch compression curve of an exemplary graph of an area under the curve useful for calculating an Energy of Compression pursuant to a Bunch Compression Method detailed herein.

Start the test and collect displacement (mm) verses force (N) data for all five cycles. Construct a graph of Force (N) versus displacement (mm) separately for all cycles. A representative curve is shown in FIG. 10a. From the curve record the Maximum Compression Force for each Cycle to the nearest 0.01N. Calculate the % Recovery between the First and Second cycle as (TD−E2)/(TD−E1)*100 where TD is the total displacement and E2 is the extension on the second compression curve that exceeds 0.02 N. Record to the nearest 0.01%. In like fashion calculate the % Recovery between the First Cycle and other cycles as (TD−Ei)/(TD−E1)*100 and report to the nearest 0.01%. Referring to FIG. 10b, calculate the Energy of Compression for Cycle 1 as the area under the compression curve (i.e., area A+B) and record to the nearest 0.1 mJ. Calculate the Energy Loss from Cycle 1 as the area between the compression and decompression curves (i.e., Area A) and report to the nearest 0.1 mJ. Calculate the Energy of Recovery for Cycle 1 as the area under the decompression curve (i.e. Area B) and report to the nearest 0.1 mJ. In like fashion, calculate the Energy of Compression (mJ), Energy Loss (mJ) and Energy of Recovery (mJ) for each of the other cycles and record to the nearest 0.1 mJ. For each sample, analyze a total of five (5) replicates and report the arithmetic mean for each parameter. All results are reported as positive numbers and specifically as dry or wet including the volume of the dose.

Examples—Part A

A. An absorbent article comprising:
  a. a primary topsheet having a body-facing surface and a garment-facing surface;
  b. a backsheet having a body-facing surface and garment-facing surface;
  c. an absorbent core having a front end portion, a central portion, and a rear end portion along its length, said core being disposed between said primary topsheet garment-facing surface and said backsheet body-facing surface, and
  wherein said article exhibits an article length of from about 371 mm to about 500 mm according to the Article Length Method; an Acquisition Time for a load of 60 ml of less than about 39 seconds according to a Speed of Acquisition with Balloon Applied Pressure Method; a dry pad thickness of between about 4.6 mm to about 12 mm according to a Pad Thickness Method; and an Energy of Recovery at a load of 30 ml of from about 5 mJ to about 11 mJ according to a Bunch Compression Method.
B. The absorbent article of paragraph A wherein said article exhibits an Acquisition Time for a load of 60 ml of less than about 37 seconds according to the Speed of Acquisition with Balloon Applied Pressure Method.
C. The absorbent article of paragraph B wherein said article exhibits an Acquisition Time for a load of 60 ml of less than about 35 seconds according to the Speed of Acquisition with Balloon Applied Pressure Method.
D. The absorbent article of paragraph A wherein said article exhibits a dry pad thickness of between about 4.8 mm to about 10 mm according to a Pad Thickness Method.
E. The absorbent article of any one of paragraph A to D wherein said article exhibits an Energy of Recovery at a load of 30 ml of from about 4.8 mJ to about 10 mJ according to a Bunch Compression Method.
F. The absorbent article of any one of paragraphs A to E wherein said core comprises a) a first laminate which includes a first superabsorbent layer disposed onto a first distribution layer and b) a second laminate which includes a second distribution layer joined to a second superabsorbent layer; wherein said first distribution layer is joined to said second distribution layer.
G. The absorbent article of paragraph F wherein said first distribution layer is joined to said second distribution layer in an offset manner along a length of the core such that said central portion of said core is formed from an overlapping joinder of said first and second laminates.
H. The absorbent article of any one of paragraphs A to G wherein said front end portion and said rear end portion are respectively disposed at opposing ends of said central portion of said core.
I. The absorbent article of any one of paragraphs A to H wherein said first and second superabsorbent layers have different cross direction widths from one another.
J. The absorbent article of paragraph I wherein said first superabsorbent layer has a lesser cross-direction width than said second superabsorbent layer.
K. The absorbent article of paragraph I wherein each of said first and second superabsorbent layers span greater than 50% of the cross-direction width of the respective adjoining first or second distribution layer.
L. The absorbent article of any one of paragraphs A to K wherein said first or second superabsorbent layers are substantially free of airfelt.
M. The absorbent article of any one of paragraphs A to L wherein said first superabsorbent layer is disposed discontinuously onto the first distribution layer.
N. The absorbent article of any one of paragraphs A to M wherein said second superabsorbent layer is disposed in a continuous pattern.
O. The absorbent article of any one of paragraphs A to N wherein said first and second laminates have cross-direction widths that are the same.
P. The absorbent article of any one of paragraphs A to O wherein said first and second laminates have cross-direction widths that are different.
Q. The absorbent article of any one of paragraphs A to P wherein said first and second laminates have machine-direction lengths that are the same.
R. The absorbent article of any one of paragraphs A to Q wherein said first and second laminates have machine-direction lengths that are different.
S. The absorbent article of any one of paragraphs A to R wherein said first and second distribution layers each comprise an airlaid material.
T. The absorbent article of any one of paragraphs A to S wherein said first and second laminates each have a first end that is complementary in shape to a respective second end of the same laminate.

U. An absorbent article comprising a chassis which comprises:
   a. a primary topsheet having a body-facing surface and a garment-facing surface;
   b. a backsheet having a body-facing surface and garment-facing surface;
   c. an absorbent core which is disposed between said primary topsheet garment-facing surface and said backsheet body-facing surface and wherein said core further comprises a first laminate having a first end which is complementary in shape to a respective second end, said first laminate comprises a first superabsorbent layer disposed onto a first distribution layer;
   wherein said article exhibits an article length of from about 371 mm to about 500 mm according to the Article Length Method; an Acquisition Time for a load of 60 ml of less than about 39 seconds according to a Speed of Acquisition with Balloon Applied Pressure Method; a dry pad thickness of between about 4.6 mm to about 12 mm according to a Pad Thickness Method; and an Energy of Recovery at a load of 30 ml of from about 5 mJ to about 11 mJ according to a Bunch Compression Method.

V. The absorbent article of paragraph W wherein said core further comprises a second laminate having a first end which is complementary in shape to its respective second end and wherein said second laminate includes a second distribution layer joined to a second superabsorbent layer; wherein said first distribution layer is joined to said second distribution layer in an offset manner along a length of the absorbent article wherein the absorbent core has a front end portion that is formed by the first end of the second laminate.

W. An absorbent article comprising a chassis which comprises:
   a. a primary topsheet having a body-facing surface and a garment-facing surface;
   b. a backsheet having a body-facing surface and garment-facing surface;
   c. an absorbent core which is disposed between said primary topsheet garment-facing surface and said backsheet body-facing surface, wherein said core comprises
      1) a first laminate which includes a first superabsorbent layer disposed onto a first distribution layer and
      2) a second laminate which includes a second distribution layer joined to a second superabsorbent layer; wherein said first distribution layer is joined to said second distribution layer along a length of the absorbent article wherein either of the first or second laminates has a larger cross-direction width than the other and
   wherein said article exhibits an article length of from about 371 mm to about 500 mm according to the Article Length Method; an Acquisition Time for a load of 60 ml of less than about 39 seconds according to a Speed of Acquisition with Balloon Applied Pressure Method; a dry pad thickness of between about 4.6 mm to about 12 mm according to a Pad Thickness Method; and an Energy of Recovery at a load of 30 ml of from about 5 mJ to about 11 mJ according to a Bunch Compression Method.

X. An absorbent article comprising a chassis which comprises:
   a. a primary topsheet having a body-facing surface and a garment-facing surface;
   b. a backsheet having a body-facing surface and garment-facing surface;
   c. an absorbent core which is disposed between said primary topsheet garment-facing surface and said backsheet body-facing surface, wherein said core comprises a first laminate which includes a first superabsorbent layer disposed discontinuously onto a first distribution layer and a second laminate which includes a second distribution layer joined to a second superabsorbent layer; wherein said first distribution layer is joined to said second distribution layer; and wherein said article exhibits an article length of from about 371 mm to about 500 mm according to the Article Length Method; an Acquisition Time for a load of 60 ml of less than about 39 seconds according to a Speed of Acquisition with Balloon Applied Pressure Method; a dry pad thickness of between about 4.6 mm to about 12 mm according to a Pad Thickness Method; and an Energy of Recovery at a load of 30 ml of from about 5 mJ to about 11 mJ according to a Bunch Compression Method.

Y. The absorbent article of claim 24 wherein said first and second laminates are joined to one another in an offset manner via their respective distribution layers.

Examples—Part B

Examples 1 and 2 are constructed in accordance with the present disclosure.

Example 1

An incontinence pad or sanitary napkin approximately 400 mm long having an hourglass shape is constructed. It has a maximum width of 119 mm and a width of 98 mm in the center of the length. The product has 2 fold lines along its length. The layers are adhesively combined using appropriate hotmelt adhesives known in the art. The outer perimeter is crimped (via heat and pressure). The pad includes the following components:

1) Primary topsheet comprising 18 gsm PE/PP bico (Sheath/core) nonwoven with hydrophilic surfactant treatment and a printed quilted pattern.

2) Secondary topsheet which is continuous in MD and 79 mm wide in the CD and formed from a material of 45% hollow, spiral PET fibers (10 dtex, 38 mm staple length), 30% Sheath/Core PE/PET Bico Fibers (5.8 dtex), 25% tri-lobal rayon fibers (3.3 dtex).

3) Absorbent core which includes at least the following two laminates.
   a) First laminate is 59 mm wide×310 mm long (on a longitudinal axis or centerline). All layers of the laminate are this full length. The first end of the first laminate exhibits nested cutting with a radius of 51.6 mm in a male connection shape complementing the shape of the second end of the same laminate which is a female connection. Hence, the first and second ends mate with one another. The first superabsorbent layer is formed from an AGM carrier material of 10 gsm SMS PP nonwoven (59 mm wide) and a layer of superabsorbent particles (AGM) which is 59 mm wide with AGM free areas approximately 10 mm square arranged throughout the first laminate are formed where a total of 4.55 g total AGM is utilized thereon. The first superabsorbent layer is joined to an airlaid material (135 gsm) comprised of pulp (82.5%), bico fiber (15%) and latex (2.5%) at 59 mm wide.
   b) A second laminate is 79 mm wide×310 mm long on a longitudinal axis or centerline. The first end of the second laminate exhibits nested cutting with a radius of 51.6 mm in a male connection shape and complementing the female connection shape of the second end of the same laminate. The second distribution layer comprises an airlaid material (135 gsm) comprised of pulp (82.5%), bico fiber (15%) and latex (2.5%) at 79 mm wide. The second superabsorbent layer comprise an AGM carrier material of 10 gsm SMS PP nonwoven which is 79 mm wide and thereon is disposed a layer of superabsorbent particles (AGM) at 71 mm wide in a continuous pattern in the MD and CD with a total of 5.7 g of AGM.

The first and second laminates are arranged with the distribution layers contacting and joined with opposing first ends of each laminate which have male connection or convex shapes forming the respective ends of the resultant pad. This pad has a total length from a front end portion to a rear end portion along the longitudinal axis of 381 mm.

4) A backsheet comprises a 14 gsm polypropylene film.

5) A barrier cuff nonwoven first cover/second cover each having a basis weight of 15 gsm (glue continuously in MD to the topsheet with a spacing of 72 mm and glued intermittently for about 87 mm at the ends of the product with a 60 mm spacing) and having an inner to inner spacing of about 54 mm (continuing to CD edges);

6) Barrier cuff elastic members or strands are formed from Lycra®. There are 2 strands per cuff each having 470 dtex stretched about 80% each and glued for 195 mm (attachment approximately 113 mm from leading and 93 mm from trailing edge). Inner to inner elastic spacing of about 61 mm and spacing of about 4 mm between each strand in each cuff.

Example 2

An incontinence pad or sanitary napkin approximately 400 mm long having an hourglass shape is constructed. It has a maximum width of 119 mm and a width of 98 mm in the center of the length. The product has 2 fold lines along its length. The layers are adhesively combined using appropriate hotmelt adhesives known in the art. The outer perimeter is crimped (via heat and pressure). The pad includes the following components:

1) Primary topsheet comprising 18 gsm PE/PP bico (Sheath/core) nonwoven with hydrophilic surfactant treatment and a printed quilted pattern.

2) Secondary topsheet which is continuous in MD and 79 mm wide in the CD and formed from a material of 45% hollow, spiral PET fibers (10 dtex, 38 mm staple length), 30% Sheath/Core PE/PET Bico Fibers (5.8 dtex), 25% tri-lobal rayon fibers (3.3 dtex).

3) Absorbent core which includes at least the following two laminates.

a) First laminate is 50.5 mm wide×339 mm long (on a longitudinal axis or centerline). All layers of the laminate are this full length. The first end of the first laminate exhibits nested cutting with a radius of 46.5 mm in a male connection shape complementing the shape of the second end of the same laminate which is a female connection. Hence, the first and second ends mate with one another. The first superabsorbent layer is formed from an AGM carrier material of 10 gsm SMS PP nonwoven 61.5 mm wide (including 11 mm wrapped around the airlaid material on one side) and a layer of superabsorbent particles (AGM) which is 38.5 mm wide with AGM free areas approximately 10 mm square arranged throughout the first laminate are formed where a total of 2.84 g total AGM is utilized thereon. The first superabsorbent layer is joined to an airlaid material (160 gsm) comprised of pulp (82.5%), bico fiber (15%) and latex (2.5%) at 50.5 mm wide.

b) A second laminate is 77.5 mm wide×339 mm long on a longitudinal axis or centerline. The first end of the second laminate exhibits nested cutting with a radius of 51.6 mm in a male connection shape and complementing the female connection shape of the second end of the same laminate. The second distribution layer comprises an airlaid material (160 gsm) comprised of pulp (82.5%), bico fiber (15%) and latex (2.5%) at 77.5 mm wide. The second superabsorbent layer comprise an AGM carrier material of 10 gsm SMS PP nonwoven which is 88.5 mm wide (including 11 mm material wrapped around back side of airlaid material) and thereon is disposed a layer of superabsorbent particles (AGM) at 65.5 mm wide in a continuous pattern in the MD and CD with a total of 6.09 g of AGM.

The first and second laminates are arranged with the distribution layers contacting and joined with opposing first ends of each laminate which have male connection or convex shapes forming the respective ends of the resultant pad. This pad has a total length from a front end portion to a rear end portion along the longitudinal axis of 381 mm.

4) A backsheet comprises a 14 gsm polypropylene film.

5) A barrier cuff nonwoven first cover/second cover each having a basis weight of 15 gsm (glue continuously in MD to the topsheet with a spacing of 72 mm and glued intermittently for about 87 mm at the ends of the product with a 60 mm spacing) and having an inner to inner spacing of about 54 mm (continuing to CD edges);

6) Barrier cuff elastic members or strands are formed from Lycra®. There are 2 strands per cuff each having 470 dtex stretched about 80% each and glued for 195 mm (attachment approximately 113 mm from leading and 93 mm from trailing edge). Inner to inner elastic spacing of about 61 mm and spacing of about 4 mm between each strand in each cuff.

The article of Examples 1 and 2 are compared to commercially available products in terms of the physical properties mentioned earlier in Table 4.

TABLE 4

| Acquisition Time vs. Load | | | | | |
|---|---|---|---|---|---|
| | Always Discreet | Poise Pads | Tena Serenity | Example 1 | Example 2 |
| Acq Time at 60 ml (s) | 39.08 | 19.18 | 17.64 | 34.24 | 24.82 |
| Pad Thickness (Dry, Unwrapped single pad) (mm) | 4.44 | 13.00 | 13.75 | 6.42 | 6.89 |
| Energy of Recovery at 20 ml (mJ) | 6.2 | 10.5 | 4.9 | 5.2 | 4.5 |
| Energy of Recovery, Dry (mJ) | 4.3 | 12.3 | 4.3 | 9.4 | 9.6 |

The above comparative pads are detailed below.

1. Poise Pads—Poise Overnight Pads: Ultimate Absorbency Long Length

2. Tena Serenity—Tena Serenity: Overnight Pads

3. Always Discreet—Always Discreet: Pads Ultimate Long Length

It is evident that the Examples of the present invention possess the various claimed physical property combinations as opposed to the commercially available incontinence products. As such, those of the presently claimed articles are able to deliver the performance, discretion, and resilience benefits as captured by the claimed characteristics whereas the commercial products are not.

What is claimed is:

1. An absorbent article comprising:
   a. a primary topsheet having a body-facing surface and a garment-facing surface;
   b. a backsheet having a body-facing surface and garment-facing surface;
   c. an absorbent core having a front end portion, a central portion, and a rear end portion along its length, said core being disposed between said primary topsheet garment-facing surface and said backsheet body-facing surface, and
   wherein said article exhibits an article length of from about 371 mm to about 500 mm according to the Article Length Method; an Acquisition Time for a load of 60 ml of less than about 39 seconds according to a Speed of Acquisition with Balloon Applied Pressure Method; a dry pad thickness of between about 4.6 mm to about 12 mm according to a Pad Thickness Method; and an Energy of Recovery at a load of 30 ml of from about 4 mJ to about 11 mJ according to a Bunch Compression Method.

2. The absorbent article of claim 1 wherein said article exhibits an Acquisition Time for a load of 60 ml of less than about 37 seconds according to the Speed of Acquisition with Balloon Applied Pressure Method.

3. The absorbent article of claim 2 wherein said article exhibits an Acquisition Time for a load of 60 ml of less than about 35 seconds according to the Speed of Acquisition with Balloon Applied Pressure Method.

4. The absorbent article of claim 1 wherein said article exhibits a dry pad thickness of between about 4.8 mm to about 10 mm according to a Pad Thickness Method.

5. The absorbent article of claim 1 wherein said article exhibits an Energy of Recovery at a load of 30 ml of from about 4.3 mJ to about 10 mJ according to a Bunch Compression Method.

6. The absorbent article of claim 1 wherein said core comprises a) a first laminate which includes a first superabsorbent layer disposed onto a first distribution layer and b) a second laminate which includes a second distribution layer joined to a second superabsorbent layer; wherein said first distribution layer is joined to said second distribution layer.

7. The absorbent article of claim 6 wherein said first distribution layer is joined to said second distribution layer in an offset manner along a length of the core such that said central portion of said core is formed from an overlapping joinder of said first and second laminates.

8. The absorbent article of claim 6, wherein said first and second superabsorbent layers have different cross direction widths from one another.

9. The absorbent article of claim 8 wherein said first superabsorbent layer has a lesser cross-direction width than said second superabsorbent layer.

10. The absorbent article of claim 6, wherein each of said first and second superabsorbent layers span greater than 50% of the cross-direction width of the respective adjoining first or second distribution layer.

11. The absorbent article of claim 6, wherein said first or second superabsorbent layers are substantially free of airfelt.

12. The absorbent article of claim 6, wherein said first superabsorbent layer is disposed discontinuously onto the first distribution layer.

13. The absorbent article of claim 6, wherein said second superabsorbent layer is disposed in a continuous pattern.

14. The absorbent article of claim 6, wherein said first and second laminates have cross-direction widths that are the same.

15. The absorbent article of claim 6, wherein said first and second laminates have cross-direction widths that are different.

16. The absorbent article of claim 6, wherein said first and second laminates have machine-direction lengths that are the same.

17. The absorbent article of claim 6, wherein said first and second laminates have machine-direction lengths that are different.

18. The absorbent article of claim 6, wherein said first and second distribution layers each comprise an airlaid material.

19. The absorbent article of claim 6, wherein said first and second laminates each have a first end that is complementary in shape to a respective second end of the same laminate.

20. The absorbent article of claim 1 wherein said front end portion and said rear end portion are respectively disposed at opposing ends of said central portion of said core.

21. An absorbent article comprising a chassis which comprises:
   a. a primary topsheet having a body-facing surface and a garment-facing surface;
   b. a backsheet having a body-facing surface and garment-facing surface;
   c. an absorbent core which is disposed between said primary topsheet garment-facing surface and said backsheet body-facing surface and wherein said core further comprises a first laminate having a first end which is complementary in shape to a respective second end, said first laminate comprises a first superabsorbent layer disposed onto a first distribution layer;
   wherein said article exhibits an article length of from about 371 mm to about 500 mm according to the Article Length Method; an Acquisition Time for a load of 60 ml of less than about 39 seconds according to a Speed of Acquisition with Balloon Applied Pressure Method; a dry pad thickness of between about 4.6 mm to about 12 mm according to a Pad Thickness Method; and an Energy of Recovery at a load of 30 ml of from about 4 mJ to about 11 mJ according to a Bunch Compression Method.

22. The absorbent article of claim 21 wherein said core further comprises a second laminate having a first end which is complementary in shape to its respective second end and wherein said second laminate includes a second distribution layer joined to a second superabsorbent layer; wherein said first distribution layer is joined to said second distribution layer in an offset manner along a length of the absorbent article wherein the absorbent core has a front end portion that is formed by the first end of the second laminate.

23. An absorbent article comprising a chassis which comprises:
   a. a primary topsheet having a body-facing surface and a garment-facing surface;
   b. a backsheet having a body-facing surface and garment-facing surface;
   c. an absorbent core which is disposed between said primary topsheet garment-facing surface and said backsheet body-facing surface, wherein said core comprises
      1) a first laminate which includes a first superabsorbent layer disposed onto a first distribution layer and
      2) a second laminate which includes a second distribution layer joined to a second superabsorbent layer; wherein said first distribution layer is joined to said second distribution layer along a length of the absorbent article wherein either of the first or second laminates has a larger cross-direction width than the other and wherein said article exhibits an article length of from about 371 mm to about 500 mm according to the Article Length Method; an Acquisition Time for a load of 60 ml of less than about 39 seconds according to a Speed of Acquisition with Balloon Applied Pressure Method; a dry pad thickness of between about 4.6 mm to about 12 mm according to a Pad Thickness Method; and an Energy of Recovery at a load of 30 ml of from about 4 mJ to about 11 mJ according to a Bunch Compression Method.

24. An absorbent article comprising a chassis which comprises:
   a. a primary topsheet having a body-facing surface and a garment-facing surface;
   b. a backsheet having a body-facing surface and garment-facing surface;
   c. an absorbent core which is disposed between said primary topsheet garment-facing surface and said backsheet body-facing surface, wherein said core comprises a first laminate which includes a first superabsorbent layer disposed discontinuously onto a first distribution layer and a second laminate which includes a second distribution layer joined to a second superabsorbent layer; wherein said first distribution layer is joined to said second distribution layer; and wherein said article exhibits an article length of from about 371 mm to about 500 mm according to the Article Length Method; an Acquisition Time for a load of 60 ml of less than about 39 seconds according to a Speed of Acquisition with Balloon Applied Pressure Method; a dry pad thickness of between about 4.6 mm to about 12 mm according to a Pad Thickness Method; and an Energy of Recovery at a load of 30 ml of from about 4 mJ to about 11 mJ according to a Bunch Compression Method.

25. The absorbent article of claim 24 wherein said first and second laminates are joined to one another in an offset manner via their respective distribution layers.

* * * * *